US012668804B2

(12) United States Patent
Zhou et al.

(10) Patent No.: US 12,668,804 B2
(45) Date of Patent: Jun. 30, 2026

(54) BIOSYNTHESIS OF ERIODICTYOL

(71) Applicant: Conagen Inc., Bedford, MA (US)

(72) Inventors: Rui Zhou, Acton, MA (US); Junying Ma, Acton, MA (US); Oliver Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 949 days.

(21) Appl. No.: 17/720,418

(22) Filed: Apr. 14, 2022

(65) Prior Publication Data

US 2022/0325290 A1 Oct. 13, 2022

Related U.S. Application Data

(63) Continuation of application No. PCT/US2020/055598, filed on Oct. 14, 2020.

(60) Provisional application No. 62/914,560, filed on Oct. 14, 2019.

(51) Int. Cl.

| | |
|---|---|
| ***C12N 15/70*** | (2006.01) |
| ***C12N 9/02*** | (2006.01) |
| ***C12N 9/06*** | (2006.01) |
| ***C12N 15/74*** | (2006.01) |
| ***C12P 17/06*** | (2006.01) |

(52) U.S. Cl.

CPC ........... *C12N 15/70* (2013.01); *C12N 9/0028* (2013.01); *C12N 9/0071* (2013.01); *C12N 15/74* (2013.01); *C12P 17/06* (2013.01); *C12Y 105/0103* (2013.01)

(58) Field of Classification Search

CPC .... C12N 15/70; C12N 9/0028; C12N 9/0071; C12N 15/74; C12P 17/06; C12Y 105/0103

See application file for complete search history.

(56) References Cited

U.S. PATENT DOCUMENTS

| | | | | |
|---|---|---|---|---|
| 5,578,476 | A * | 11/1996 | Zenno | C12N 9/0036 435/189 |
| 2010/0047887 | A1* | 2/2010 | Achkar | C12P 7/22 435/156 |
| 2010/0107277 | A1* | 4/2010 | Brugliera | C12N 9/0073 800/315 |
| 2018/0135029 | A1* | 5/2018 | Wessjohann | C12N 9/1007 |
| 2019/0048374 | A1 | 2/2019 | Zhou et al. | |

FOREIGN PATENT DOCUMENTS

| | | |
|---|---|---|
| WO | WO 2006/010117 A2 | 1/2006 |
| WO | WO 2019/032235 A2 | 2/2019 |
| WO | WO 2020/077367 A1 | 4/2020 |
| WO | PCT/US2020/055598 | 3/2021 |

OTHER PUBLICATIONS

Amor et al., Biotransformation of naringenin to eriodictyol by *Saccharomyces cerevisiea* functionally expressing flavonoid 3' hydroxylase. Nat Prod Commun. Dec. 2010;5(12):1893-8.

(Continued)

*Primary Examiner* — Jonathan M Hurst

(74) *Attorney, Agent, or Firm* — Wolf, Greenfield & Sacks, P.C.

(57) ABSTRACT

The present invention relates to methods and transformed host cells for the production of eriodictyol from naringenin via bioconversion.

21 Claims, 5 Drawing Sheets

Specification includes a Sequence Listing.

Naringenin

Eriodictyol

(56) References Cited

OTHER PUBLICATIONS

Extended European Search Report for Application No. 20876827.5, mailed Oct. 12, 2022.

Lee et al., Production of bioactive hydroxyflavones by using monooxygenase from Saccharothrix espanaensis. J Biotechnol. Apr. 20, 2014:176:11-7. doi: 10.1016/j.jbiotec.2014.02.002. Epub Feb. 19, 2014.

No Author Listed, NCBI accession No. WP_107054157.1. Pyoverdin chromophore biosynthetic protein pvcC [Streptomyces sclerotialus]. Mar. 31, 2018. 1 page.

No Author Listed, Ebi accession No. UNIPROT:A0A212TVJ3. SubName: Full=4-hydroxyphenylacetate 3-monooxygenase {ECO:0000313|EMBL:SNC70028.1}. Oct. 25, 2017.

* cited by examiner

SEQUENCE LISTING

<160> NUMBER OF SEQ ID NOS: 20

<210> SEQ ID NO 1
<211> LENGTH: 1512
<212> TYPE: DNA
<213> ORGANISM: Artificial Sequence
<220> FEATURE:
<223> OTHER INFORMATION: SsPvcC-M196Y mutant

<400> SEQUENCE: 1
atgacgggcg ccgaatatct ggattcgctg cgtgatggcc gtgccgtcta tattcacggc 60
gaacgcgtcc gcgatgtcac cgcgcatccg gccttccgta acagcgcgcg tagtctggcg 120
cagctgtatg atgtgctgca tgaaccggat tcgcgtggcg ttctgagcgt cccgaccgat 180
accggtaatg gcggttttac gcacccgttt ttcaaaaccg cgcgtagcgc cggtgatctg 240
gtggcagccc gcgatgcaat tgtggcctgg cagcgtcttg tttacggttg gatgggtcgt 300
acgccggatt ataaagcagc attcttcggt acgcttgaag ccaacgccga tttctatggc 360
ccgttccgtg ataacgcact ggcatggtat cgtcgtgcac aggaacgcgt gttgtatttc 420
aaccatgcga tcgtgcatcc gccggtcgat cgcgatcgcc cggccgatcg cacggcggat 480
gtgtgcgtcc acgtggaaga agaaacggat gccggccttg ttgtttcggg tgcgaaagtt 540
gtcgcgacca gcagcgccct gacgaatgcc aatctgattg cacactacgg cttaccgctg 600
cgtgataaac gctttggcgc catgttcacc gtgccgatgg atagcccggg cctgaaactg 660
ttctgtcgta ccagttatga aatgcatgcc gcggtcttag gctcgccgtt tgattacccg 720
ttaagcagcc gccttgatga aaatgattca atcatggttc ttgatcgtgt tttagtgccg 780
tgggaaaacg tgtttatgta tgatgccgcc agcgcgaacg cgtttgcgac ccgcagcggt 840
ttcctggaac gttttacctt tcatggctgt acgcgcttag cggtgaaact ggattttatt 900
gccggttgcc tgctgaaagc agttgaagtg accggcacca gcggcttccg tggtgtgcag 960
gcccagattg gcgaagtttt aaactggcgc gatatgtttt ggggtatgtc agatgcaatg 1020
gcgaaatcgc cgacggattg gcacaatggt gcggtccagc cgaatctgaa ctatggcctg 1080
gcctaccgca ccttcatggg cattggttac ccgcgtatcc gtgaaatcat tcagcagacc 1140

-continued

```
attggctcgg gtctgattta tttaaatagt cacgcaagcg attggaaaaa tccggaagtt   1200

cgtccgtact tagatcgcta cctgcgcggt agtcgtggtg ttgaagcgat cgatcgcgtt   1260

aaactgctta aactgctgtg ggattgcgtg ggcacggaat ttgcgggccg tcacgaactt   1320

tatgaacgca attacggtgg cgatcatgaa ggtattcgcg tgcagaccct gttgagttat   1380

caggcgcgcg gtcaggcgga tgcgcttaaa ggctttgccg atcagtgtat gtcagaatac   1440

gatctggatg gctggacccg cccggattta ttcggtccag gtgatttacc tagaccagct   1500

actggagcgt aa                                                        1512


<210> SEQ ID NO 2
<211> LENGTH: 503
<212> TYPE: PRT
<213> ORGANISM: Artificial Sequence
<220> FEATURE:
<223> OTHER INFORMATION: SsPvcC-M196Y mutant

<400> SEQUENCE: 2

Met Thr Gly Ala Glu Tyr Leu Asp Ser Leu Arg Asp Gly Arg Ala Val
1               5                   10                  15

Tyr Ile His Gly Glu Arg Val Arg Asp Val Thr Ala His Pro Ala Phe
            20                  25                  30

Arg Asn Ser Ala Arg Ser Leu Ala Gln Leu Tyr Asp Val Leu His Glu
        35                  40                  45

Pro Asp Ser Arg Gly Val Leu Ser Val Pro Thr Asp Thr Gly Asn Gly
    50                  55                  60

Gly Phe Thr His Pro Phe Phe Lys Thr Ala Arg Ser Ala Gly Asp Leu
65                  70                  75                  80

Val Ala Ala Arg Asp Ala Ile Val Ala Trp Gln Arg Leu Val Tyr Gly
                85                  90                  95

Trp Met Gly Arg Thr Pro Asp Tyr Lys Ala Ala Phe Phe Gly Thr Leu
            100                 105                 110

Glu Ala Asn Ala Asp Phe Tyr Gly Pro Phe Arg Asp Asn Ala Leu Ala
        115                 120                 125

Trp Tyr Arg Arg Ala Gln Glu Arg Val Leu Tyr Phe Asn His Ala Ile
    130                 135                 140

Val His Pro Pro Val Asp Arg Asp Arg Pro Ala Asp Arg Thr Ala Asp
145                 150                 155                 160

Val Cys Val His Val Glu Glu Glu Thr Asp Ala Gly Leu Val Val Ser
                165                 170                 175

Gly Ala Lys Val Val Ala Thr Ser Ser Ala Leu Thr Asn Ala Asn Leu
            180                 185                 190

Ile Ala His Tyr Gly Leu Pro Leu Arg Asp Lys Arg Phe Gly Ala Met
        195                 200                 205

Phe Thr Val Pro Met Asp Ser Pro Gly Leu Lys Leu Phe Cys Arg Thr
    210                 215                 220

Ser Tyr Glu Met His Ala Ala Val Leu Gly Ser Pro Phe Asp Tyr Pro
225                 230                 235                 240

Leu Ser Ser Arg Leu Asp Glu Asn Asp Ser Ile Met Val Leu Asp Arg
                245                 250                 255

Val Leu Val Pro Trp Glu Asn Val Phe Met Tyr Asp Ala Ala Ser Ala
            260                 265                 270

Asn Ala Phe Ala Thr Arg Ser Gly Phe Leu Glu Arg Phe Thr Phe His
        275                 280                 285

Gly Cys Thr Arg Leu Ala Val Lys Leu Asp Phe Ile Ala Gly Cys Leu
```

```
    290                 295                 300

Leu Lys Ala Val Glu Val Thr Gly Thr Ser Gly Phe Arg Gly Val Gln
305                 310                 315                 320

Ala Gln Ile Gly Glu Val Leu Asn Trp Arg Asp Met Phe Trp Gly Met
                325                 330                 335

Ser Asp Ala Met Ala Lys Ser Pro Thr Asp Trp His Asn Gly Ala Val
            340                 345                 350

Gln Pro Asn Leu Asn Tyr Gly Leu Ala Tyr Arg Thr Phe Met Gly Ile
        355                 360                 365

Gly Tyr Pro Arg Ile Arg Glu Ile Ile Gln Gln Thr Ile Gly Ser Gly
    370                 375                 380

Leu Ile Tyr Leu Asn Ser His Ala Ser Asp Trp Lys Asn Pro Glu Val
385                 390                 395                 400

Arg Pro Tyr Leu Asp Arg Tyr Leu Arg Gly Ser Arg Gly Val Glu Ala
                405                 410                 415

Ile Asp Arg Val Lys Leu Leu Lys Leu Leu Trp Asp Cys Val Gly Thr
            420                 425                 430

Glu Phe Ala Gly Arg His Glu Leu Tyr Glu Arg Asn Tyr Gly Gly Asp
        435                 440                 445

His Glu Gly Ile Arg Val Gln Thr Leu Leu Ser Tyr Gln Ala Arg Gly
    450                 455                 460

Gln Ala Asp Ala Leu Lys Gly Phe Ala Asp Gln Cys Met Ser Glu Tyr
465                 470                 475                 480

Asp Leu Asp Gly Trp Thr Arg Pro Asp Leu Phe Gly Pro Gly Asp Leu
                485                 490                 495

Pro Arg Pro Ala Thr Gly Ala
            500
```

<210> SEQ ID NO 3
<211> LENGTH: 1563
<212> TYPE: DNA
<213> ORGANISM: Artificial Sequence
<220> FEATURE:
<223> OTHER INFORMATION: SsPvcC-M196Y-Tag

<400> SEQUENCE: 3

```
atgacgaccg ctagtggtac caatgcagat gtccagaatg gcgtccgccc gatgacgggc     60

gccgaatatc tggattcgct gcgtgatggc cgtgccgtct atattcacgg cgaacgcgtc    120

cgcgatgtca ccgcgcatcc ggccttccgt aacagcgcgc gtagtctggc gcagctgtat    180

gatgtgctgc atgaaccgga ttcgcgtggc gttctgagcg tcccgaccga taccggtaat    240

ggcggtttta cgcacccgtt tttcaaaacc gcgcgtagcg ccggtgatct ggtggcagcc    300

cgcgatgcaa ttgtggcctg gcagcgtctt gtttacggtt ggatgggtcg tacgccggat    360

tataaagcag cattcttcgg tacgcttgaa gccaacgccg atttctatgg cccgttccgt    420

gataacgcac tggcatggta tcgtcgtgca caggaacgcg tgttgtattt caaccatgcg    480

atcgtgcatc cgccggtcga tcgcgatcgc ccggccgatc gcacggcgga tgtgtgcgtc    540

cacgtggaag aagaaacgga tgccggcctt gttgtttcgg gtgcgaaagt tgtcgcgacc    600

agcagcgccc tgacgaatgc caatctgatt gcacactacg gcttaccgct gcgtgataaa    660

cgctttggcg ccatgttcac cgtgccgatg gatagcccgg gcctgaaact gttctgtcgt    720

accagttatg aaatgcatgc cgcggtctta ggctcgccgt ttgattaccc gttaagcagc    780

cgccttgatg aaaatgattc aatcatggtt cttgatcgtg ttttagtgcc gtgggaaaac    840
```

-continued

```
gtgtttatgt atgatgccgc cagcgcgaac gcgtttgcga cccgcagcgg tttcctggaa    900

cgttttacct ttcatggctg tacgcgctta gcggtgaaac tggattttat tgccggttgc    960

ctgctgaaag cagttgaagt gaccggcacc agcggcttcc gtggtgtgca ggcccagatt   1020

ggcgaagttt taaactggcg cgatatgttt tggggtatgt cagatgcaat ggcgaaatcg   1080

ccgacggatt ggcacaatgg tgcggtccag ccgaatctga actatggcct ggcctaccgc   1140

accttcatgg gcattggtta cccgcgtatc cgtgaaatca ttcagcagac cattggctcg   1200

ggtctgattt atttaaatag tcacgcaagc gattggaaaa atccggaagt tcgtccgtac   1260

ttagatcgct acctgcgcgg tagtcgtggt gttgaagcga tcgatcgcgt taaactgctt   1320

aaactgctgt gggattgcgt gggcacggaa tttgcgggcc gtcacgaact ttatgaacgc   1380

aattacggtg gcgatcatga aggtattcgc gtgcagaccc tgttgagtta tcaggcgcgc   1440

ggtcaggcgg atgcgcttaa aggctttgcc gatcagtgta tgtcagaata cgatctggat   1500

ggctggaccc gcccggattt attcggtcca ggtgatttac ctagaccagc tactggagcg   1560

taa                                                                 1563


<210> SEQ ID NO 4
<211> LENGTH: 520
<212> TYPE: PRT
<213> ORGANISM: Artificial Sequence
<220> FEATURE:
<223> OTHER INFORMATION: SsPvcC-M196Y-Tag mutant

<400> SEQUENCE: 4

Met Thr Thr Ala Ser Gly Thr Asn Ala Asp Val Gln Asn Gly Val Arg
1               5                   10                  15

Pro Met Thr Gly Ala Glu Tyr Leu Asp Ser Leu Arg Asp Gly Arg Ala
            20                  25                  30

Val Tyr Ile His Gly Glu Arg Val Arg Asp Val Thr Ala His Pro Ala
        35                  40                  45

Phe Arg Asn Ser Ala Arg Ser Leu Ala Gln Leu Tyr Asp Val Leu His
    50                  55                  60

Glu Pro Asp Ser Arg Gly Val Leu Ser Val Pro Thr Asp Thr Gly Asn
65                  70                  75                  80

Gly Gly Phe Thr His Pro Phe Phe Lys Thr Ala Arg Ser Ala Gly Asp
                85                  90                  95

Leu Val Ala Ala Arg Asp Ala Ile Val Ala Trp Gln Arg Leu Val Tyr
            100                 105                 110

Gly Trp Met Gly Arg Thr Pro Asp Tyr Lys Ala Ala Phe Phe Gly Thr
        115                 120                 125

Leu Glu Ala Asn Ala Asp Phe Tyr Gly Pro Phe Arg Asp Asn Ala Leu
    130                 135                 140

Ala Trp Tyr Arg Arg Ala Gln Glu Arg Val Leu Tyr Phe Asn His Ala
145                 150                 155                 160

Ile Val His Pro Pro Val Asp Arg Asp Arg Pro Ala Asp Arg Thr Ala
                165                 170                 175

Asp Val Cys Val His Val Glu Glu Glu Thr Asp Ala Gly Leu Val Val
            180                 185                 190

Ser Gly Ala Lys Val Val Ala Thr Ser Ser Ala Leu Thr Asn Ala Asn
        195                 200                 205

Leu Ile Ala His Tyr Gly Leu Pro Leu Arg Asp Lys Arg Phe Gly Ala
    210                 215                 220

Met Phe Thr Val Pro Met Asp Ser Pro Gly Leu Lys Leu Phe Cys Arg
```

-continued

```
225                 230                 235                 240

Thr Ser Tyr Glu Met His Ala Ala Val Leu Gly Ser Pro Phe Asp Tyr
                245                 250                 255

Pro Leu Ser Ser Arg Leu Asp Glu Asn Asp Ser Ile Met Val Leu Asp
            260                 265                 270

Arg Val Leu Val Pro Trp Glu Asn Val Phe Met Tyr Asp Ala Ala Ser
        275                 280                 285

Ala Asn Ala Phe Ala Thr Arg Ser Gly Phe Leu Glu Arg Phe Thr Phe
    290                 295                 300

His Gly Cys Thr Arg Leu Ala Val Lys Leu Asp Phe Ile Ala Gly Cys
305                 310                 315                 320

Leu Leu Lys Ala Val Glu Val Thr Gly Thr Ser Gly Phe Arg Gly Val
                325                 330                 335

Gln Ala Gln Ile Gly Glu Val Leu Asn Trp Arg Asp Met Phe Trp Gly
            340                 345                 350

Met Ser Asp Ala Met Ala Lys Ser Pro Thr Asp Trp His Asn Gly Ala
        355                 360                 365

Val Gln Pro Asn Leu Asn Tyr Gly Leu Ala Tyr Arg Thr Phe Met Gly
    370                 375                 380

Ile Gly Tyr Pro Arg Ile Arg Glu Ile Ile Gln Gln Thr Ile Gly Ser
385                 390                 395                 400

Gly Leu Ile Tyr Leu Asn Ser His Ala Ser Asp Trp Lys Asn Pro Glu
                405                 410                 415

Val Arg Pro Tyr Leu Asp Arg Tyr Leu Arg Gly Ser Arg Gly Val Glu
            420                 425                 430

Ala Ile Asp Arg Val Lys Leu Leu Lys Leu Leu Trp Asp Cys Val Gly
        435                 440                 445

Thr Glu Phe Ala Gly Arg His Glu Leu Tyr Glu Arg Asn Tyr Gly Gly
    450                 455                 460

Asp His Glu Gly Ile Arg Val Gln Thr Leu Leu Ser Tyr Gln Ala Arg
465                 470                 475                 480

Gly Gln Ala Asp Ala Leu Lys Gly Phe Ala Asp Gln Cys Met Ser Glu
                485                 490                 495

Tyr Asp Leu Asp Gly Trp Thr Arg Pro Asp Leu Phe Gly Pro Gly Asp
            500                 505                 510

Leu Pro Arg Pro Ala Thr Gly Ala
        515                 520
```

<210> SEQ ID NO 5
<211> LENGTH: 1563
<212> TYPE: DNA
<213> ORGANISM: Artificial Sequence
<220> FEATURE:
<223> OTHER INFORMATION: SsPvcC-G315H+Tag mutant

<400> SEQUENCE: 5

```
atgacgaccg ctagtggtac caatgcagat gtccagaatg gcgtccgccc gatgacgggc     60

gccgaatatc tggattcgct gcgtgatggc cgtgccgtct atattcacgg cgaacgcgtc    120

cgcgatgtca ccgcgcatcc ggccttccgt aacagcgcgc gtagtctggc gcagctgtat    180

gatgtgctgc atgaaccgga ttcgcgtggc gttctgagcg tcccgaccga taccggtaat    240

ggcggtttta cgcacccgtt tttcaaaacc gcgcgtagcg ccggtgatct ggtggcagcc    300

cgcgatgcaa ttgtggcctg gcagcgtctt gtttacggtt ggatgggtcg tacgccggat    360

tataaagcag cattcttcgg tacgcttgaa gccaacgccg atttctatgg cccgttccgt    420
```

-continued

```
gataacgcac tggcatggta tcgtcgtgca caggaacgcg tgttgtattt caaccatgcg    480

atcgtgcatc cgccggtcga tcgcgatcgc ccggccgatc gcacggcgga tgtgtgcgtc    540

cacgtggaag aagaaacgga tgccggcctt gttgtttcgg gtgcgaaagt tgtcgcgacc    600

agcagcgccc tgacgaatgc caatctgatt gcacacatgg gcttaccgct gcgtgataaa    660

cgctttggcg ccatgttcac cgtgccgatg gatagcccgg gcctgaaact gttctgtcgt    720

accagttatg aaatgcatgc cgcggtctta ggctcgccgt ttgattaccc gttaagcagc    780

cgccttgatg aaaatgattc aatcatggtt cttgatcgtg ttttagtgcc gtgggaaaac    840

gtgtttatgt atgatgccgc cagcgcgaac gcgtttgcga cccgcagcgg tttcctggaa    900

cgttttacct ttcatggctg tacgcgctta gcggtgaaac tggattttat tgccggttgc    960

ctgctgaaag cagttgaagt gaccggcacc agccacttcc gtggtgtgca ggcccagatt   1020

ggcgaagttt taaactggcg cgatatgttt tggggtatgt cagatgcaat ggcgaaatcg   1080

ccgacggatt ggcacaatgg tgcggtccag ccgaatctga actatggcct ggcctaccgc   1140

accttcatgg gcattggtta cccgcgtatc cgtgaaatca ttcagcagac cattggctcg   1200

ggtctgattt atttaaatag tcacgcaagc gattggaaaa atccggaagt tcgtccgtac   1260

ttagatcgct acctgcgcgg tagtcgtggt gttgaagcga tcgatcgcgt taaactgctt   1320

aaactgctgt gggattgcgt gggcacggaa tttgcgggcc gtcacgaact ttatgaacgc   1380

aattacggtg gcgatcatga aggtattcgc gtgcagaccc tgttgagtta tcaggcgcgc   1440

ggtcaggcgg atgcgcttaa aggctttgcc gatcagtgta tgtcagaata cgatctggat   1500

ggctggaccc gcccggattt attcggtcca ggtgatttac ctagaccagc tactggagcg   1560

taa                                                                 1563
```

<210> SEQ ID NO 6
<211> LENGTH: 520
<212> TYPE: PRT
<213> ORGANISM: Artificial Sequence
<220> FEATURE:
<223> OTHER INFORMATION: SsPvcC-G315H+Tag mutant

<400> SEQUENCE: 6

```
Met Thr Thr Ala Ser Gly Thr Asn Ala Asp Val Gln Asn Gly Val Arg
1               5                   10                  15

Pro Met Thr Gly Ala Glu Tyr Leu Asp Ser Leu Arg Asp Gly Arg Ala
            20                  25                  30

Val Tyr Ile His Gly Glu Arg Val Arg Asp Val Thr Ala His Pro Ala
        35                  40                  45

Phe Arg Asn Ser Ala Arg Ser Leu Ala Gln Leu Tyr Asp Val Leu His
    50                  55                  60

Glu Pro Asp Ser Arg Gly Val Leu Ser Val Pro Thr Asp Thr Gly Asn
65                  70                  75                  80

Gly Gly Phe Thr His Pro Phe Phe Lys Thr Ala Arg Ser Ala Gly Asp
                85                  90                  95

Leu Val Ala Ala Arg Asp Ala Ile Val Ala Trp Gln Arg Leu Val Tyr
            100                 105                 110

Gly Trp Met Gly Arg Thr Pro Asp Tyr Lys Ala Ala Phe Phe Gly Thr
        115                 120                 125

Leu Glu Ala Asn Ala Asp Phe Tyr Gly Pro Phe Arg Asp Asn Ala Leu
    130                 135                 140

Ala Trp Tyr Arg Arg Ala Gln Glu Arg Val Leu Tyr Phe Asn His Ala
```

-continued

```
145                 150                 155                 160

Ile Val His Pro Pro Val Asp Arg Asp Arg Pro Ala Asp Arg Thr Ala
                165                 170                 175

Asp Val Cys Val His Val Glu Glu Glu Thr Asp Ala Gly Leu Val Val
            180                 185                 190

Ser Gly Ala Lys Val Val Ala Thr Ser Ser Ala Leu Thr Asn Ala Asn
        195                 200                 205

Leu Ile Ala His Met Gly Leu Pro Leu Arg Asp Lys Arg Phe Gly Ala
    210                 215                 220

Met Phe Thr Val Pro Met Asp Ser Pro Gly Leu Lys Leu Phe Cys Arg
225                 230                 235                 240

Thr Ser Tyr Glu Met His Ala Ala Val Leu Gly Ser Pro Phe Asp Tyr
                245                 250                 255

Pro Leu Ser Ser Arg Leu Asp Glu Asn Asp Ser Ile Met Val Leu Asp
            260                 265                 270

Arg Val Leu Val Pro Trp Glu Asn Val Phe Met Tyr Asp Ala Ala Ser
        275                 280                 285

Ala Asn Ala Phe Ala Thr Arg Ser Gly Phe Leu Glu Arg Phe Thr Phe
    290                 295                 300

His Gly Cys Thr Arg Leu Ala Val Lys Leu Asp Phe Ile Ala Gly Cys
305                 310                 315                 320

Leu Leu Lys Ala Val Glu Val Thr Gly Thr Ser His Phe Arg Gly Val
                325                 330                 335

Gln Ala Gln Ile Gly Glu Val Leu Asn Trp Arg Asp Met Phe Trp Gly
            340                 345                 350

Met Ser Asp Ala Met Ala Lys Ser Pro Thr Asp Trp His Asn Gly Ala
        355                 360                 365

Val Gln Pro Asn Leu Asn Tyr Gly Leu Ala Tyr Arg Thr Phe Met Gly
    370                 375                 380

Ile Gly Tyr Pro Arg Ile Arg Glu Ile Ile Gln Gln Thr Ile Gly Ser
385                 390                 395                 400

Gly Leu Ile Tyr Leu Asn Ser His Ala Ser Asp Trp Lys Asn Pro Glu
                405                 410                 415

Val Arg Pro Tyr Leu Asp Arg Tyr Leu Arg Gly Ser Arg Gly Val Glu
            420                 425                 430

Ala Ile Asp Arg Val Lys Leu Leu Lys Leu Leu Trp Asp Cys Val Gly
        435                 440                 445

Thr Glu Phe Ala Gly Arg His Glu Leu Tyr Glu Arg Asn Tyr Gly Gly
    450                 455                 460

Asp His Glu Gly Ile Arg Val Gln Thr Leu Leu Ser Tyr Gln Ala Arg
465                 470                 475                 480

Gly Gln Ala Asp Ala Leu Lys Gly Phe Ala Asp Gln Cys Met Ser Glu
                485                 490                 495

Tyr Asp Leu Asp Gly Trp Thr Arg Pro Asp Leu Phe Gly Pro Gly Asp
            500                 505                 510

Leu Pro Arg Pro Ala Thr Gly Ala
        515                 520
```

<210> SEQ ID NO 7
<211> LENGTH: 1563
<212> TYPE: DNA
<213> ORGANISM: Artificial Sequence
<220> FEATURE:
<223> OTHER INFORMATION: SsPvcC-D214N+Tag mutant

<400> SEQUENCE: 7

```
atgacgaccg ctagtggtac caatgcagat gtccagaatg gcgtccgccc gatgacgggc     60
gccgaatatc tggattcgct gcgtgatggc cgtgccgtct atattcacgg cgaacgcgtc    120
cgcgatgtca ccgcgcatcc ggccttccgt aacagcgcgc gtagtctggc gcagctgtat    180
gatgtgctgc atgaaccgga ttcgcgtggc gttctgagcg tcccgaccga taccggtaat    240
ggcggtttta cgcacccgtt tttcaaaacc gcgcgtagcg ccggtgatct ggtggcagcc    300
cgcgatgcaa ttgtggcctg gcagcgtctt gtttacggtt ggatgggtcg tacgccggat    360
tataaagcag cattcttcgg tacgcttgaa gccaacgccg atttctatgg cccgttccgt    420
gataacgcac tggcatggta tcgtcgtgca caggaacgcg tgttgtattt caaccatgcg    480
atcgtgcatc cgccggtcga tcgcgatcgc ccggccgatc gcacggcgga tgtgtgcgtc    540
cacgtggaag aagaaacgga tgccggcctt gttgtttcgg gtgcgaaagt tgtcgcgacc    600
agcagcgccc tgacgaatgc caatctgatt gcacacatgg gcttaccgct gcgtgataaa    660
cgctttggcg ccatgttcac cgtgccgatg aatagcccgg gcctgaaact gttctgtcgt    720
accagttatg aaatgcatgc cgcggtctta ggctcgccgt ttgattaccc gttaagcagc    780
cgccttgatg aaaatgattc aatcatggtt cttgatcgtg ttttagtgcc gtgggaaaac    840
gtgtttatgt atgatgccgc cagcgcgaac gcgtttgcga cccgcagcgg tttcctggaa    900
cgttttacct ttcatggctg tacgcgctta gcggtgaaac tggattttat tgccggttgc    960
ctgctgaaag cagttgaagt gaccggcacc agccatttcc gtggtgtgca ggcccagatt   1020
ggcgaagttt taaactggcg cgatatgttt tggggtatgt cagatgcaat ggcgaaatcg   1080
ccgacggatt ggcacaatgg tgcggtccag ccgaatctga actatggcct ggcctaccgc   1140
accttcatgg gcattggtta cccgcgtatc cgtgaaatca ttcagcagac cattggctcg   1200
ggtctgattt atttaaatag tcacgcaagc gattggaaaa atccggaagt tcgtccgtac   1260
ttagatcgct acctgcgcgg tagtcgtggt gttgaagcga tcgatcgcgt taaactgctt   1320
aaactgctgt gggattgcgt gggcacggaa tttgcgggcc gtcacgaact ttatgaacgc   1380
aattacggtg gcgatcatga aggtattcgc gtgcagaccc tgttgagtta tcaggcgcgc   1440
ggtcaggcgg atgcgcttaa aggctttgcc gatcagtgta tgtcagaata cgatctggat   1500
ggctggaccc gcccggattt attcggtcca ggtgatttac ctagaccagc tactggagcg   1560
taa                                                                 1563
```

<210> SEQ ID NO 8
<211> LENGTH: 520
<212> TYPE: PRT
<213> ORGANISM: Artificial Sequence
<220> FEATURE:
<223> OTHER INFORMATION: SsPvcC-D214N+Tag mutant

<400> SEQUENCE: 8

```
Met Thr Thr Ala Ser Gly Thr Asn Ala Asp Val Gln Asn Gly Val Arg
1               5                   10                  15

Pro Met Thr Gly Ala Glu Tyr Leu Asp Ser Leu Arg Asp Gly Arg Ala
            20                  25                  30

Val Tyr Ile His Gly Glu Arg Val Arg Asp Val Thr Ala His Pro Ala
        35                  40                  45

Phe Arg Asn Ser Ala Arg Ser Leu Ala Gln Leu Tyr Asp Val Leu His
    50                  55                  60

Glu Pro Asp Ser Arg Gly Val Leu Ser Val Pro Thr Asp Thr Gly Asn
```

-continued

```
65                  70                  75                  80

Gly Gly Phe Thr His Pro Phe Phe Lys Thr Ala Arg Ser Ala Gly Asp
                85                  90                  95

Leu Val Ala Ala Arg Asp Ala Ile Val Ala Trp Gln Arg Leu Val Tyr
            100                 105                 110

Gly Trp Met Gly Arg Thr Pro Asp Tyr Lys Ala Ala Phe Phe Gly Thr
        115                 120                 125

Leu Glu Ala Asn Ala Asp Phe Tyr Gly Pro Phe Arg Asp Asn Ala Leu
    130                 135                 140

Ala Trp Tyr Arg Arg Ala Gln Glu Arg Val Leu Tyr Phe Asn His Ala
145                 150                 155                 160

Ile Val His Pro Pro Val Asp Arg Asp Arg Pro Ala Asp Arg Thr Ala
                165                 170                 175

Asp Val Cys Val His Val Glu Glu Glu Thr Asp Ala Gly Leu Val Val
            180                 185                 190

Ser Gly Ala Lys Val Val Ala Thr Ser Ser Ala Leu Thr Asn Ala Asn
        195                 200                 205

Leu Ile Ala His Met Gly Leu Pro Leu Arg Asp Lys Arg Phe Gly Ala
    210                 215                 220

Met Phe Thr Val Pro Met Asn Ser Pro Gly Leu Lys Leu Phe Cys Arg
225                 230                 235                 240

Thr Ser Tyr Glu Met His Ala Ala Val Leu Gly Ser Pro Phe Asp Tyr
                245                 250                 255

Pro Leu Ser Ser Arg Leu Asp Glu Asn Asp Ser Ile Met Val Leu Asp
            260                 265                 270

Arg Val Leu Val Pro Trp Glu Asn Val Phe Met Tyr Asp Ala Ala Ser
        275                 280                 285

Ala Asn Ala Phe Ala Thr Arg Ser Gly Phe Leu Glu Arg Phe Thr Phe
    290                 295                 300

His Gly Cys Thr Arg Leu Ala Val Lys Leu Asp Phe Ile Ala Gly Cys
305                 310                 315                 320

Leu Leu Lys Ala Val Glu Val Thr Gly Thr Ser Gly Phe Arg Gly Val
                325                 330                 335

Gln Ala Gln Ile Gly Glu Val Leu Asn Trp Arg Asp Met Phe Trp Gly
            340                 345                 350

Met Ser Asp Ala Met Ala Lys Ser Pro Thr Asp Trp His Asn Gly Ala
        355                 360                 365

Val Gln Pro Asn Leu Asn Tyr Gly Leu Ala Tyr Arg Thr Phe Met Gly
    370                 375                 380

Ile Gly Tyr Pro Arg Ile Arg Glu Ile Ile Gln Gln Thr Ile Gly Ser
385                 390                 395                 400

Gly Leu Ile Tyr Leu Asn Ser His Ala Ser Asp Trp Lys Asn Pro Glu
                405                 410                 415

Val Arg Pro Tyr Leu Asp Arg Tyr Leu Arg Gly Ser Arg Gly Val Glu
            420                 425                 430

Ala Ile Asp Arg Val Lys Leu Leu Lys Leu Leu Trp Asp Cys Val Gly
        435                 440                 445

Thr Glu Phe Ala Gly Arg His Glu Leu Tyr Glu Arg Asn Tyr Gly Gly
    450                 455                 460

Asp His Glu Gly Ile Arg Val Gln Thr Leu Leu Ser Tyr Gln Ala Arg
465                 470                 475                 480

Gly Gln Ala Asp Ala Leu Lys Gly Phe Ala Asp Gln Cys Met Ser Glu
                485                 490                 495
```

Tyr Asp Leu Asp Gly Trp Thr Arg Pro Asp Leu Phe Gly Pro Gly Asp
500 505 510

Leu Pro Arg Pro Ala Thr Gly Ala
515 520

<210> SEQ ID NO 9
<211> LENGTH: 1563
<212> TYPE: DNA
<213> ORGANISM: Artificial Sequence
<220> FEATURE:
<223> OTHER INFORMATION: SsPvcC+Tag

<400> SEQUENCE: 9
atgacgaccg ctagtggtac caatgcagat gtccagaatg gcgtccgccc gatgacgggc 60
gccgaatatc tggattcgct gcgtgatggc cgtgccgtct atattcacgg cgaacgcgtc 120
cgcgatgtca ccgcgcatcc ggccttccgt aacagcgcgc gtagtctggc gcagctgtat 180
gatgtgctgc atgaaccgga ttcgcgtggc gttctgagcg tcccgaccga taccggtaat 240
ggcggtttta cgcacccgtt tttcaaaacc gcgcgtagcg ccggtgatct ggtggcagcc 300
cgcgatgcaa ttgtggcctg gcagcgtctt gtttacggtt ggatgggtcg tacgccggat 360
tataaagcag cattcttcgg tacgcttgaa gccaacgccg atttctatgg cccgttccgt 420
gataacgcac tggcatggta tcgtcgtgca caggaacgcg tgttgtattt caaccatgcg 480
atcgtgcatc cgccggtcga tcgcgatcgc ccggccgatc gcacggcgga tgtgtgcgtc 540
cacgtggaag aagaaacgga tgccggcctt gttgtttcgg gtgcgaaagt tgtcgcgacc 600
agcagcgccc tgacgaatgc caatctgatt gcacacatgg gcttaccgct gcgtgataaa 660
cgctttggcg ccatgttcac cgtgccgatg gatagcccgg gcctgaaact gttctgtcgt 720
accagttatg aaatgcatgc cgcggtctta ggctcgccgt ttgattaccc gttaagcagc 780
cgccttgatg aaaatgattc aatcatggtt cttgatcgtg ttttagtgcc gtgggaaaac 840
gtgtttatgt atgatgccgc cagcgcgaac gcgtttgcga cccgcagcgg tttcctggaa 900
cgttttacct ttcatggctg tacgcgctta gcggtgaaac tggattttat tgccggttgc 960
ctgctgaaag cagttgaagt gaccggcacc agcggcttcc gtggtgtgca ggcccagatt 1020
ggcgaagttt taaactggcg cgatatgttt tggggtatgt cagatgcaat ggcgaaatcg 1080
ccgacggatt ggcacaatgg tgcggtccag ccgaatctga actatggcct ggcctaccgc 1140
accttcatgg gcattggtta cccgcgtatc cgtgaaatca ttcagcagac cattggctcg 1200
ggtctgattt atttaaatag tcacgcaagc gattggaaaa atccggaagt tcgtccgtac 1260
ttagatcgct acctgcgcgg tagtcgtggt gttgaagcga tcgatcgcgt taaactgctt 1320
aaactgctgt gggattgcgt gggcacggaa tttgcgggcc gtcacgaact ttatgaacgc 1380
aattacggtg gcgatcatga aggtattcgc gtgcagaccc tgttgagtta tcaggcgcgc 1440
ggtcaggcgg atgcgcttaa aggctttgcc gatcagtgta tgtcagaata cgatctggat 1500
ggctggaccc gcccggattt attcggtcca ggtgatttac ctagaccagc tactggagcg 1560
taa 1563

<210> SEQ ID NO 10
<211> LENGTH: 520
<212> TYPE: PRT
<213> ORGANISM: Artificial Sequence
<220> FEATURE:
<223> OTHER INFORMATION: SsPvcC+Tag

<400> SEQUENCE: 10

```
Met Thr Thr Ala Ser Gly Thr Asn Ala Asp Val Gln Asn Gly Val Arg
1               5                   10                  15

Pro Met Thr Gly Ala Glu Tyr Leu Asp Ser Leu Arg Asp Gly Arg Ala
            20                  25                  30

Val Tyr Ile His Gly Glu Arg Val Arg Asp Val Thr Ala His Pro Ala
        35                  40                  45

Phe Arg Asn Ser Ala Arg Ser Leu Ala Gln Leu Tyr Asp Val Leu His
    50                  55                  60

Glu Pro Asp Ser Arg Gly Val Leu Ser Val Pro Thr Asp Thr Gly Asn
65                  70                  75                  80

Gly Gly Phe Thr His Pro Phe Phe Lys Thr Ala Arg Ser Ala Gly Asp
                85                  90                  95

Leu Val Ala Ala Arg Asp Ala Ile Val Ala Trp Gln Arg Leu Val Tyr
            100                 105                 110

Gly Trp Met Gly Arg Thr Pro Asp Tyr Lys Ala Ala Phe Phe Gly Thr
        115                 120                 125

Leu Glu Ala Asn Ala Asp Phe Tyr Gly Pro Phe Arg Asp Asn Ala Leu
    130                 135                 140

Ala Trp Tyr Arg Arg Ala Gln Glu Arg Val Leu Tyr Phe Asn His Ala
145                 150                 155                 160

Ile Val His Pro Pro Val Asp Arg Asp Arg Pro Ala Asp Arg Thr Ala
                165                 170                 175

Asp Val Cys Val His Val Glu Glu Glu Thr Asp Ala Gly Leu Val Val
            180                 185                 190

Ser Gly Ala Lys Val Val Ala Thr Ser Ser Ala Leu Thr Asn Ala Asn
        195                 200                 205

Leu Ile Ala His Met Gly Leu Pro Leu Arg Asp Lys Arg Phe Gly Ala
    210                 215                 220

Met Phe Thr Val Pro Met Asp Ser Pro Gly Leu Lys Leu Phe Cys Arg
225                 230                 235                 240

Thr Ser Tyr Glu Met His Ala Ala Val Leu Gly Ser Pro Phe Asp Tyr
                245                 250                 255

Pro Leu Ser Ser Arg Leu Asp Glu Asn Asp Ser Ile Met Val Leu Asp
            260                 265                 270

Arg Val Leu Val Pro Trp Glu Asn Val Phe Met Tyr Asp Ala Ala Ser
        275                 280                 285

Ala Asn Ala Phe Ala Thr Arg Ser Gly Phe Leu Glu Arg Phe Thr Phe
    290                 295                 300

His Gly Cys Thr Arg Leu Ala Val Lys Leu Asp Phe Ile Ala Gly Cys
305                 310                 315                 320

Leu Leu Lys Ala Val Glu Val Thr Gly Thr Ser Gly Phe Arg Gly Val
                325                 330                 335

Gln Ala Gln Ile Gly Glu Val Leu Asn Trp Arg Asp Met Phe Trp Gly
            340                 345                 350

Met Ser Asp Ala Met Ala Lys Ser Pro Thr Asp Trp His Asn Gly Ala
        355                 360                 365

Val Gln Pro Asn Leu Asn Tyr Gly Leu Ala Tyr Arg Thr Phe Met Gly
    370                 375                 380

Ile Gly Tyr Pro Arg Ile Arg Glu Ile Ile Gln Gln Thr Ile Gly Ser
385                 390                 395                 400

Gly Leu Ile Tyr Leu Asn Ser His Ala Ser Asp Trp Lys Asn Pro Glu
                405                 410                 415
```

-continued

```
Val Arg Pro Tyr Leu Asp Arg Tyr Leu Arg Gly Ser Arg Gly Val Glu
            420                 425                 430

Ala Ile Asp Arg Val Lys Leu Leu Lys Leu Leu Trp Asp Cys Val Gly
        435                 440                 445

Thr Glu Phe Ala Gly Arg His Glu Leu Tyr Glu Arg Asn Tyr Gly Gly
    450                 455                 460

Asp His Glu Gly Ile Arg Val Gln Thr Leu Leu Ser Tyr Gln Ala Arg
465                 470                 475                 480

Gly Gln Ala Asp Ala Leu Lys Gly Phe Ala Asp Gln Cys Met Ser Glu
                485                 490                 495

Tyr Asp Leu Asp Gly Trp Thr Arg Pro Asp Leu Phe Gly Pro Gly Asp
            500                 505                 510

Leu Pro Arg Pro Ala Thr Gly Ala
        515                 520


<210> SEQ ID NO 11
<211> LENGTH: 1512
<212> TYPE: DNA
<213> ORGANISM: Streptomyces sclerotialus

<400> SEQUENCE: 11

atgacgggcg ccgaatatct ggattcgctg cgtgatggcc gtgccgtcta tattcacggc     60

gaacgcgtcc gcgatgtcac cgcgcatccg gccttccgta acagcgcgcg tagtctggcg    120

cagctgtatg atgtgctgca tgaaccggat tcgcgtggcg ttctgagcgt cccgaccgat    180

accggtaatg gcggttttac gcacccgttt ttcaaaaccg cgcgtagcgc cggtgatctg    240

gtggcagccc gcgatgcaat tgtggcctgg cagcgtcttg tttacggttg gatgggtcgt    300

acgccggatt ataaagcagc attcttcggt acgcttgaag ccaacgccga tttctatggc    360

ccgttccgtg ataacgcact ggcatggtat cgtcgtgcac aggaacgcgt gttgtatttc    420

aaccatgcga tcgtgcatcc gccggtcgat cgcgatcgcc cggccgatcg cacggcggat    480

gtgtgcgtcc acgtggaaga agaaacggat gccggccttg ttgtttcggg tgcgaaagtt    540

gtcgcgacca gcagcgccct gacgaatgcc aatctgattg cacacatggg cttaccgctg    600

cgtgataaac gctttggcgc catgttcacc gtgccgatgg atagcccggg cctgaaactg    660

ttctgtcgta ccagttatga aatgcatgcc gcggtcttag gctcgccgtt tgattacccg    720

ttaagcagcc gccttgatga aaatgattca atcatggttc ttgatcgtgt tttagtgccg    780

tgggaaaacg tgtttatgta tgatgccgcc agcgcgaacg cgtttgcgac ccgcagcggt    840

ttcctggaac gttttacctt tcatggctgt acgcgcttag cggtgaaact ggattttatt    900

gccggttgcc tgctgaaagc agttgaagtg accggcacca gcggcttccg tggtgtgcag    960

gcccagattg gcgaagtttt aaactggcgc gatatgtttt ggggtatgtc agatgcaatg   1020

gcgaaatcgc cgacggattg gcacaatggt gcggtccagc cgaatctgaa ctatggcctg   1080

gcctaccgca ccttcatggg cattggttac ccgcgtatcc gtgaaatcat tcagcagacc   1140

attggctcgg gtctgattta tttaaatagt cacgcaagcg attggaaaaa tccggaagtt   1200

cgtccgtact tagatcgcta cctgcgcggt agtcgtggtg ttgaagcgat cgatcgcgtt   1260

aaactgctta aactgctgtg ggattgcgtg ggcacggaat ttgcgggccg tcacgaactt   1320

tatgaacgca attacggtgg cgatcatgaa ggtattcgcg tgcagaccct gttgagttat   1380

caggcgcgcg gtcaggcgga tgcgcttaaa ggctttgccg atcagtgtat gtcagaatac   1440

gatctggatg gctggacccg cccggattta ttcggtccag gtgatttacc tagaccagct   1500
```

actgggagcgt aa 1512

<210> SEQ ID NO 12
<211> LENGTH: 503
<212> TYPE: PRT
<213> ORGANISM: Streptomyces sclerotialus

<400> SEQUENCE: 12

```
Met Thr Gly Ala Glu Tyr Leu Asp Ser Leu Arg Asp Gly Arg Ala Val
1               5                   10                  15

Tyr Ile His Gly Glu Arg Val Arg Asp Val Thr Ala His Pro Ala Phe
            20                  25                  30

Arg Asn Ser Ala Arg Ser Leu Ala Gln Leu Tyr Asp Val Leu His Glu
        35                  40                  45

Pro Asp Ser Arg Gly Val Leu Ser Val Pro Thr Asp Thr Gly Asn Gly
    50                  55                  60

Gly Phe Thr His Pro Phe Phe Lys Thr Ala Arg Ser Ala Gly Asp Leu
65                  70                  75                  80

Val Ala Ala Arg Asp Ala Ile Val Ala Trp Gln Arg Leu Val Tyr Gly
                85                  90                  95

Trp Met Gly Arg Thr Pro Asp Tyr Lys Ala Ala Phe Phe Gly Thr Leu
            100                 105                 110

Glu Ala Asn Ala Asp Phe Tyr Gly Pro Phe Arg Asp Asn Ala Leu Ala
        115                 120                 125

Trp Tyr Arg Arg Ala Gln Glu Arg Val Leu Tyr Phe Asn His Ala Ile
    130                 135                 140

Val His Pro Pro Val Asp Arg Asp Arg Pro Ala Asp Arg Thr Ala Asp
145                 150                 155                 160

Val Cys Val His Val Glu Glu Glu Thr Asp Ala Gly Leu Val Val Ser
                165                 170                 175

Gly Ala Lys Val Val Ala Thr Ser Ser Ala Leu Thr Asn Ala Asn Leu
            180                 185                 190

Ile Ala His Met Gly Leu Pro Leu Arg Asp Lys Arg Phe Gly Ala Met
        195                 200                 205

Phe Thr Val Pro Met Asp Ser Pro Gly Leu Lys Leu Phe Cys Arg Thr
    210                 215                 220

Ser Tyr Glu Met His Ala Ala Val Leu Gly Ser Pro Phe Asp Tyr Pro
225                 230                 235                 240

Leu Ser Ser Arg Leu Asp Glu Asn Asp Ser Ile Met Val Leu Asp Arg
                245                 250                 255

Val Leu Val Pro Trp Glu Asn Val Phe Met Tyr Asp Ala Ala Ser Ala
            260                 265                 270

Asn Ala Phe Ala Thr Arg Ser Gly Phe Leu Glu Arg Phe Thr Phe His
        275                 280                 285

Gly Cys Thr Arg Leu Ala Val Lys Leu Asp Phe Ile Ala Gly Cys Leu
    290                 295                 300

Leu Lys Ala Val Glu Val Thr Gly Thr Ser Gly Phe Arg Gly Val Gln
305                 310                 315                 320

Ala Gln Ile Gly Glu Val Leu Asn Trp Arg Asp Met Phe Trp Gly Met
                325                 330                 335

Ser Asp Ala Met Ala Lys Ser Pro Thr Asp Trp His Asn Gly Ala Val
            340                 345                 350

Gln Pro Asn Leu Asn Tyr Gly Leu Ala Tyr Arg Thr Phe Met Gly Ile
        355                 360                 365
```

Gly Tyr Pro Arg Ile Arg Glu Ile Ile Gln Gln Thr Ile Gly Ser Gly
    370                 375                 380

Leu Ile Tyr Leu Asn Ser His Ala Ser Asp Trp Lys Asn Pro Glu Val
385                 390                 395                 400

Arg Pro Tyr Leu Asp Arg Tyr Leu Arg Gly Ser Arg Gly Val Glu Ala
                405                 410                 415

Ile Asp Arg Val Lys Leu Leu Lys Leu Leu Trp Asp Cys Val Gly Thr
            420                 425                 430

Glu Phe Ala Gly Arg His Glu Leu Tyr Glu Arg Asn Tyr Gly Gly Asp
        435                 440                 445

His Glu Gly Ile Arg Val Gln Thr Leu Leu Ser Tyr Gln Ala Arg Gly
    450                 455                 460

Gln Ala Asp Ala Leu Lys Gly Phe Ala Asp Gln Cys Met Ser Glu Tyr
465                 470                 475                 480

Asp Leu Asp Gly Trp Thr Arg Pro Asp Leu Phe Gly Pro Gly Asp Leu
                485                 490                 495

Pro Arg Pro Ala Thr Gly Ala
            500

<210> SEQ ID NO 13
<211> LENGTH: 510
<212> TYPE: DNA
<213> ORGANISM: Saccharothrix espanaensis

<400> SEQUENCE: 13
atgatgaccg tttatgatag cgcactgaca atggaagaaa ccaccctgcg tgatgcaatg 60
agccgttttg caaccggtgt tagcgttgtt accgttggtg gtgaacatac acatggtatg 120
accgcaaatg cctttacctg tgttagcctg gatccgcctc tggttctgtg ttgtgttgca 180
cgtaaagcaa ccatgcatgc agcaattgaa ggtgcacgtc gttttgcagt tagcgttatg 240
ggtggtgatc aagaacgtac cgcacgttat tttgcagata aacgtcgtcc gcgtggtcgt 300
gcacagtttg atgttgttga ttggcagcct ggtccgcata caggtgcacc gctgctgagc 360
ggtgcgctgg catggctgga atgtgaagtt gcacagtggc atgaaggtgg cgatcatacc 420
atttttctgg gtcgtgttct gggttgtcgt cgtggtccgg atagtccggc actgctgttt 480
tatggtagcg attttcatca gatccgctaa 510

<210> SEQ ID NO 14
<211> LENGTH: 169
<212> TYPE: PRT
<213> ORGANISM: Saccharothrix espanaensis

<400> SEQUENCE: 14

Met Met Thr Val Tyr Asp Ser Ala Leu Thr Met Glu Glu Thr Thr Leu
1               5                   10                  15

Arg Asp Ala Met Ser Arg Phe Ala Thr Gly Val Ser Val Val Thr Val
            20                  25                  30

Gly Gly Glu His Thr His Gly Met Thr Ala Asn Ala Phe Thr Cys Val
        35                  40                  45

Ser Leu Asp Pro Pro Leu Val Leu Cys Cys Val Ala Arg Lys Ala Thr
    50                  55                  60

Met His Ala Ala Ile Glu Gly Ala Arg Arg Phe Ala Val Ser Val Met
65                  70                  75                  80

Gly Gly Asp Gln Glu Arg Thr Ala Arg Tyr Phe Ala Asp Lys Arg Arg
                85                  90                  95

-continued

```
Pro Arg Gly Arg Ala Gln Phe Asp Val Val Asp Trp Gln Pro Gly Pro
            100                 105                 110

His Thr Gly Ala Pro Leu Leu Ser Gly Ala Leu Ala Trp Leu Glu Cys
        115                 120                 125

Glu Val Ala Gln Trp His Glu Gly Gly Asp His Thr Ile Phe Leu Gly
    130                 135                 140

Arg Val Leu Gly Cys Arg Arg Gly Pro Asp Ser Pro Ala Leu Leu Phe
145                 150                 155                 160

Tyr Gly Ser Asp Phe His Gln Ile Arg
                165


<210> SEQ ID NO 15
<211> LENGTH: 561
<212> TYPE: DNA
<213> ORGANISM: Pseudomonas fluorescens

<400> SEQUENCE: 15

atgaatgcag caaccgaaac caaagttcat gatctgctgg atgccgaagg tcgtgatgtt      60

cgtgatgcac gtgaactgcg taatgttctg ggtcagtttg caaccggtgt taccgttatt     120

accacccgta ccgcagatgg tcgtaatgtt ggtgtgaccg caaatagctt tagcagcctg     180

agcctgagtc cggcactggt tctgtggtca ctggcacgta ccgcaccgag cctgaaagtt     240

ttttgtagcg caagccattt tgccattaat gtgctgggtg cacatcagct gcatctgagc     300

gaacagtttg cacgtgccgc agcagataaa tttgccggtg ttgcacatag ttatggtaaa     360

gcgggtgcac cggttctgga tgatgttgtt gcagttctgg tttgccgtaa tgttacccag     420

tatgaaggtg gtgatcatct gatttttatc ggcgaaattg agcagtatcg ttatagcggt     480

gcagaaccgc tggtttttca tgcaggtcag tatcgtggtc tgggtagcaa tcgtgcagaa     540

agcgttctga aacatgaata a                                               561


<210> SEQ ID NO 16
<211> LENGTH: 186
<212> TYPE: PRT
<213> ORGANISM: Pseudomonas fluorescens

<400> SEQUENCE: 16

Met Asn Ala Ala Thr Glu Thr Lys Val His Asp Leu Leu Asp Ala Glu
1               5                   10                  15

Gly Arg Asp Val Arg Asp Ala Arg Glu Leu Arg Asn Val Leu Gly Gln
            20                  25                  30

Phe Ala Thr Gly Val Thr Val Ile Thr Thr Arg Thr Ala Asp Gly Arg
        35                  40                  45

Asn Val Gly Val Thr Ala Asn Ser Phe Ser Ser Leu Ser Leu Ser Pro
    50                  55                  60

Ala Leu Val Leu Trp Ser Leu Ala Arg Thr Ala Pro Ser Leu Lys Val
65                  70                  75                  80

Phe Cys Ser Ala Ser His Phe Ala Ile Asn Val Leu Gly Ala His Gln
                85                  90                  95

Leu His Leu Ser Glu Gln Phe Ala Arg Ala Ala Ala Asp Lys Phe Ala
            100                 105                 110

Gly Val Ala His Ser Tyr Gly Lys Ala Gly Ala Pro Val Leu Asp Asp
        115                 120                 125

Val Val Ala Val Leu Val Cys Arg Asn Val Thr Gln Tyr Glu Gly Gly
    130                 135                 140
```

-continued

```
Asp His Leu Ile Phe Ile Gly Glu Ile Glu Gln Tyr Arg Tyr Ser Gly
145                 150                 155                 160

Ala Glu Pro Leu Val Phe His Ala Gly Gln Tyr Arg Gly Leu Gly Ser
                165                 170                 175

Asn Arg Ala Glu Ser Val Leu Lys His Glu
            180                 185


<210> SEQ ID NO 17
<211> LENGTH: 513
<212> TYPE: DNA
<213> ORGANISM: Escherichia coli

<400> SEQUENCE: 17

atgcaattag atgaacaacg cctgcgcttt cgtgacgcaa tggccagcct gtcggcagcg      60

gtaaatatta tcaccaccga gggcgacgcc ggacaatgcg ggattacggc aacggccgtc     120

tgctcggtca cggatacacc accatcgctg atggtgtgca ttaacgccaa cagtgcgatg     180

aacccggttt ttcagggcaa cggtaagttg tgcgtcaacg tcctcaacca tgagcaggaa     240

ctgatggcac gccacttcgc gggcatgaca ggcatggcga tggaagagcg ttttagcctc     300

tcatgctggc aaaaaggtcc gctggcgcag ccggtgctaa aaggttcgct ggccagtctt     360

gaaggtgaga tccgcgatgt gcaggcaatt ggcacacatc tggtgtatct ggtggagatt     420

aaaaacatca tcctcagtgc agaaggtcac ggacttatct actttaaacg ccgtttccat     480

ccggtgatgc tggaaatgga agctgcgatt taa                                 513


<210> SEQ ID NO 18
<211> LENGTH: 170
<212> TYPE: PRT
<213> ORGANISM: Escherichia coli

<400> SEQUENCE: 18

Met Gln Leu Asp Glu Gln Arg Leu Arg Phe Arg Asp Ala Met Ala Ser
1               5                   10                  15

Leu Ser Ala Ala Val Asn Ile Ile Thr Thr Glu Gly Asp Ala Gly Gln
            20                  25                  30

Cys Gly Ile Thr Ala Thr Ala Val Cys Ser Val Thr Asp Thr Pro Pro
        35                  40                  45

Ser Leu Met Val Cys Ile Asn Ala Asn Ser Ala Met Asn Pro Val Phe
    50                  55                  60

Gln Gly Asn Gly Lys Leu Cys Val Asn Val Leu Asn His Glu Gln Glu
65                  70                  75                  80

Leu Met Ala Arg His Phe Ala Gly Met Thr Gly Met Ala Met Glu Glu
                85                  90                  95

Arg Phe Ser Leu Ser Cys Trp Gln Lys Gly Pro Leu Ala Gln Pro Val
            100                 105                 110

Leu Lys Gly Ser Leu Ala Ser Leu Glu Gly Glu Ile Arg Asp Val Gln
        115                 120                 125

Ala Ile Gly Thr His Leu Val Tyr Leu Val Glu Ile Lys Asn Ile Ile
    130                 135                 140

Leu Ser Ala Glu Gly His Gly Leu Ile Tyr Phe Lys Arg Arg Phe His
145                 150                 155                 160

Pro Val Met Leu Glu Met Glu Ala Ala Ile
                165                 170


<210> SEQ ID NO 19
<211> LENGTH: 51
```

-continued

```
<212> TYPE: DNA
<213> ORGANISM: Artificial Sequence
<220> FEATURE:
<223> OTHER INFORMATION: N-terminal tag

<400> SEQUENCE: 19

atgacgaccg ctagtggtac caatgcagat gtccagaatg gcgtccgccc g            51


<210> SEQ ID NO 20
<211> LENGTH: 17
<212> TYPE: PRT
<213> ORGANISM: Artificial Sequence
<220> FEATURE:
<223> OTHER INFORMATION: N-terminal tag

<400> SEQUENCE: 20

Met Thr Thr Ala Ser Gly Thr Asn Ala Asp Val Gln Asn Gly Val Arg
1               5                   10                  15

Pro
```

BIOSYNTHESIS OF ERIODICTYOL

RELATED APPLICATIONS

This application is a continuation of International Patent Application No. PCT/US2020/055598, filed Oct. 14, 2020, which claims the benefit under 35 U.S.C. § 119 (e) to U.S. Provisional Application No. 62/914,560, filed Oct. 14, 2019. The entire contents of these applications are incorporated herein by reference in their entirety.

REFERENCE TO AN ELECTRONIC SEQUENCE LISTING

This application contains a Sequence Listing which has been submitted in ASCII format via EFS-Web and is hereby incorporated by reference in its entirety. Said ASCII copy, created on Apr. 12, 2022, is named C149770080US01-SEQ-ZJG and is 47,955 bytes in size.

FIELD OF THE INVENTION

The field of the invention relates to methods and transformed host cells useful in the production of 3'-hydroxylated flavonoids, e.g., eriodictyol from precursor molecules such as naringenin. More specifically, the present invention relates to the production of eriodictyol from naringenin via in vivo enzymatic conversion.

BACKGROUND OF THE INVENTION

Flavonoids are secondary metabolites synthesized through the phenylpropanoid pathway in plants (Winkel-Shirley, 2001). They play special roles in plant growth and development. They also have been shown to possess special important biological activities and pharmaceutical properties. They are known to have a variety of multi-beneficial medicinal and chemo-preventive effects on human health, and can be used as antioxidants, anti-bacterials, anti-inflammatory agents, and have demonstrated anticancer properties.

Eriodictyol is a flavonoid extracted from Yerba Santa (*Eriodictyon californicum*) with a bitter masking property (Ley et al 2005).

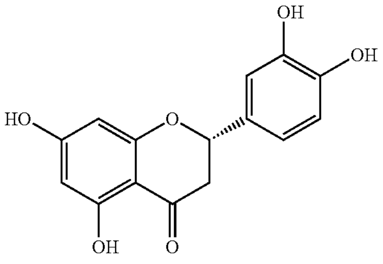 [SMILES: O=C1C[C@@H](c2ccc(O)c(O)c2)Oc2cc(O)cc(O)c21]

In a sensory study, it was demonstrated to decrease the bitter taste of caffeine significantly without exhibiting intrinsic strong flavors or taste characteristics. Thus, eriodictyol has great potential in the production of food, drink and medicine.

As secondary metabolites, many flavonoids including eriodictyol often are produced in small amounts in particular plant species, which hampers their cost-effective isolation and broad application. Moreover, some of these species are endangered in their natural habitats, thus further limiting the availability of some plant metabolites. Meanwhile, regio-specific hydroxylation of complex aromatic compounds is still quite challenging for chemical synthesis. Therefore, more attention has been given to biosynthesis of flavonoids or biotransformation through biocatalysis with microorganism (Cao et al. 2015; Lin et al 2014).

Naringenin is a colorless flavanone, which is a type of flavonoid. Naringenin has the skeleton structure of a flavanone with three hydroxy groups at the 4', 5, and 7 carbons. It may be found both in the aglycone form, naringenin, or in its glycosidic form, naringin, which has the addition of the disaccharide neohesperidose attached via a glycosidic linkage at carbon 7. Naringin can be easily converted to naringenin by hydrolation to release the glucosidic group.

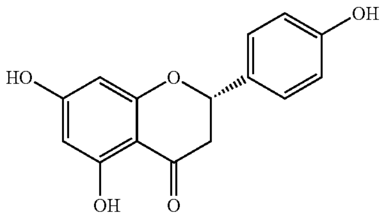 [SMILES: O=C1C[C@@H](c2ccc(O)cc2)Oc2cc(O)cc(O)c21]

Naringenin and its glycoside has been found in a variety of herbs and fruits, including citrus fruits. Citrus plants belonging to the family Rutaceae which include fruits such as orange, mandarin, lime, lemon, sour orange and grapefruit appear as a well-known promising source of multiple beneficial nutrients for human beings. Processing of citrus by-products provides a rich source of naringenin and naringin, owing to the large amount of peel produced.

Eriodictyol can be derived by the hydroxylation of naringenin in plants by the catalysis of flavonoid 3'-hydroxylase (F3'H) in plants, a cytochrome P450-dependent monooxygenase (Brugliera et al., 1999; Kaltenbach et al. 1999). In past decades, biocatalytic hydroxylation of naringenin was achieved due to the identification and engineering of some cytochrome P450 hydroxylases from plants and microorganisms (Kasai et al., 2009; Amor et al. 2010; Chu et al. 2016). However, as most P450 hydroxylases are membrane-bound proteins, their activities depend on P450-reductase and heme biosynthesis, and therefore, the functional expression of P450s in prokaryotic system is challenging (Oeda et al., 1985). Recently some efforts have been taken to identify non-P450 hydroxylase for the bioconversion of naringenin to eriodictyol. Lin and Yan (2014) found HpaBC, which was initially identified as a two-component monooxygenase that catalyzes the orthohydroxylation of 4-hydroxyphenylacetate in *Escherichia coli*, could hydroxylate naringenin to eriodictyol (Lin and Yan 2014). However, the reported titers of eriodictyol via these non-P450 hydroxylase are low for scale-up production use. Lee et al. (2014) showed SAM5, a monooxygenase from *Saccharothrix espanaensis* catalyzing the hydroxylation of caffeic acid to ferulic acid, had the activity toward naringenin. The expressed SAM5 enzyme alone showed low activity to flavonoid in *E. coli* cells. Co-expression of a P450 reductase was one way to increase activity. However, the stimulation of hydroxylation of flavonoids through this approach is limited, and only ~34-50% enhancement was observed (Lee et al 2014). In co-owned, co-pending U.S. Patent Application Publication No. 2019/0048374, the inventors have reported that by engineering *Escherichia coli* cells to overexpress a flavin reductase together with SAM5 could catalyze the conversion of naringenin to eriodictyol with high efficiency (FIG. 1).

However, it is challenging to employ SAM5 in the bioconversion of naringenin to eriodictyol in industrial applications because SAM5 has been shown to catalyze multi-hydroxylation of some flavonoids. The art therefore seeks alternative flavonoid 3'-hydroxylases capable of converting flavonoids, such as naringenin, to 3'-hydroxylated flavonoids, such as eriodictyol, yet do not further hydroxylate the 3'-hydroxylated flavonoids to multi-hydroxylated products.

SUMMARY OF THE INVENTION

The present disclosure addresses the problems described above by providing a novel flavonoid 3'-hydroxylase and related variants that are capable of converting flavonoids (e.g., naringenin) to 3'-hydroxylated flavonoids (e.g., eriodictyol) without further hydroxylating the 3'-hydroxylated flavonoids to multi-hydroxylated products. The present disclosure further encompasses biosynthetic production of 3'-hydroxylated flavonoids (e.g., eriodictyol) from the corresponding flavonoids (e.g., naringenin) by incubating transformed host cells that include recombinant polynucleotide sequences that encode such novel flavonoid 3' hydroxylases. Isolated host cells that have been transformed with recombinant polynucleotide sequences that encode such flavonoid 3' hydroxylases also are within the scope of the present teachings.

Accordingly, in one aspect, the present teachings provide a method of producing a 3'-hydroxylated flavonoid, where such method includes incubating a transformed host cell in a suitable medium that includes a flavonoid. In various embodiments, the transformed host cell comprises a synthetic or recombinant nucleic acid molecule that includes a first polynucleotide sequence that encodes a flavonoid 3'-hydroxylase. The transformed host cell is grown under conditions that induce the expression of the flavonoid 3'-hydroxylase, then further incubated with the flavonoid to produce the 3'-hydroxylated flavonoid.

More specifically, said flavonoid 3'-hydroxylase can include an N-terminal tag having the amino acid sequence of MTTASGTNADVQNGVRP (SEQ ID NO: 20). Said flavonoid 3'-hydroxylase can be the putative pyoverdine chromophore biosynthetic protein C from *Streptomyces sclerotialus* having the amino acid sequence of SEQ ID NO: 12 or a variant thereof. More specifically, the flavonoid 3'-hydroxylase can include an amino acid sequence having at least 80%, 85%, 90%, 95%, 96%, 97%, 98%, 99% sequence identity to the amino acid sequence of SEQ ID NO: 12. In some embodiments, the flavonoid 3'-hydroxylase can include an amino acid sequence having at least 80% sequence identity to the amino acid sequence of SEQ ID NO: 12 and the amino acid sequence of SEQ ID NO: 20. In certain embodiments, the flavonoid 3'-hydroxylase can include one or more mutations selected from the group consisting of M196Y, G315H, and D214N compared to the amino acid sequence of SEQ ID NO: 12. Each of these mutants can include an N-terminal tag having the amino acid sequence of MTTASGTNADVQNGVRP. In some embodiments, the flavonoid 3'-hydroxylase can comprise the amino acid sequence of SEQ ID NO: 2, SEQ ID NO: 4, SEQ ID NO: 6, SEQ ID NO: 8, or SEQ ID NO: 10. In certain embodiments, the flavonoid 3'-hydroxylase can consist of the amino acid sequence of SEQ ID NO: 2, SEQ ID NO: 4, SEQ ID NO: 6, SEQ ID NO: 8, or SEQ ID NO: 10. In some embodiments, the first polynucleotide sequence encoding the flavonoid 3'-hydroxylase can comprise a nucleic acid sequence having at least 80%, 85%, 90%, 95%, 96%, 97%, 98%, 99% sequence identity to the nucleic acid sequence of SEQ ID NO: 1, SEQ ID NO: 3, SEQ ID NO: 5, SEQ ID NO: 7, or SEQ ID NO: 9. In certain embodiments, the first polynucleotide sequence encoding the flavonoid 3'-hydroxylase can comprise the nucleic acid sequence of SEQ ID NO: 1, SEQ ID NO: 3, SEQ ID NO: 5, SEQ ID NO: 7, or SEQ ID NO: 9. In particular embodiments, the first polynucleotide sequence encoding the flavonoid 3'-hydroxylase can consist of the nucleic acid sequence of SEQ ID NO: 1, SEQ ID NO: 3, SEQ ID NO: 5, SEQ ID NO: 7, or SEQ ID NO: 9.

In various embodiments, the synthetic or recombinant nucleic acid molecule can include a second polynucleotide sequence that encodes a flavin reductase. In some embodiments, the flavin reductase can be a *Saccharothrix espanaensis* flavin reductase, a *Pseudomonas fluorescens* flavin reductase, or the reductase subunit of a 4-hydroxyphenylacetate 3-monooxygenase (HpaC) from *E. coli*. The flavin reductase can be a polypeptide comprising the amino acid sequence of SEQ ID NO: 14, SEQ ID NO: 16, or SEQ ID NO: 18. The second polynucleotide sequence encoding the flavin reductase can be selected from the group consisting of SEQ ID NO: 13, SEQ ID NO: 15, or SEQ ID NO: 17.

In various embodiments, the transformed host cell can be cultured at a temperature range of about 25° C. to about 40° C. The culture medium can include one or more amino acids, and optionally glucose and/or an antibiotic. The transformed host cell can be cultured for a sufficient period of time until stable cell growth is reached. This typically is referred to as the cell growth phase and can be between about 15 to about 18 hours. The flavonoid substrate can be added only after stable cell growth is reached, or about 15 to about 18 hours after the transformed host cell is added to the culture medium. Once the flavonoid substrate is added, the bioconversion phase begins. Such bioconversion phase can take place between about 15 to 18 hours after the transformed host cell is added to the culture medium and can last until about 40 to 60 hours after the transformed host cell is added to the culture medium.

Various 3-hydroxylated flavonoids can be produced according to the present method. Such 3-hydroxylated flavonoids can have the generic structure of one of the following:

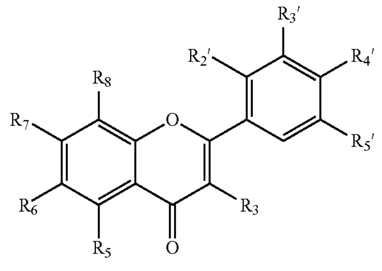

Flavone

-continued

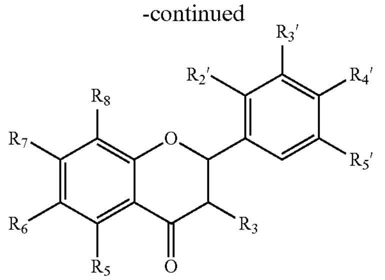

Flavanone where $R_{3'}$ is OH, and each of $R_{2'}$, $R_{4'}$, $R_{5'}$, $R_3$, $R_5$, $R_6$, $R_7$, and $R_8$ independently, can be selected from the group consisting of H, OH, and $OCH_3$. The corresponding flavonoid substrate also can have the generic structure of:

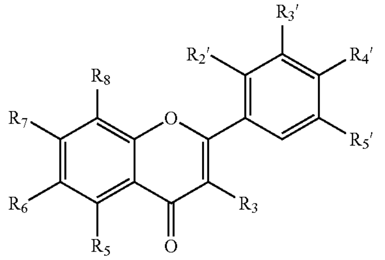

Flavone

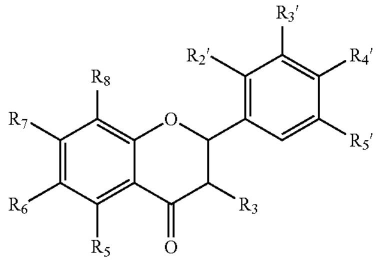

Flavanone where $R_{3'}$ is H, and each of $R_{2'}$, $R_{4'}$, $R_{5'}$, $R_3$, $R_5$, $R_6$, $R_7$, and $R_8$ corresponds to the definition of $R_{2'}$, $R_{4'}$, $R_{5'}$, $R_3$, $R_5$, $R_6$, $R_7$, and $R_8$ of the 3-hydroxylated flavonoid.

In preferred embodiments, the present method relates to a method of producing the 3'-hydroxylated flavanone eriodictyol (where $R_{3'}$ is OH; $R_{4'}$, $R_5$ and $R_7$ are OH; and $R_{2'}$, $R_{5'}$, $R_3$, $R_6$ and $R_5$ are H), from the flavonone naringenin (where $R_{3'}$ is H; $R_{4'}$, $R_5$ and $R_7$ are OH; and $R_{2'}$, $R_{5'}$, $R_3$, $R_6$ and $R_8$ are H). In preferred embodiments, the flavonoid 3'-hydroxylase encoded by the first polynucleotide sequence can include the amino acid sequence of SEQ ID NO: 4. In further preferred embodiments, the flavin reductase encoded by the second polynucleotide sequence can include the amino acid sequence of SEQ ID NO: 14.

In another aspect, the present teachings relate to an isolated recombinant host cell transformed with a nucleic acid construct comprising a first polynucleotide sequence that encodes an exogenous flavonoid 3'-hydroxylase. In some embodiments, the nucleic acid construct can further include a second polynucleotide sequence that encodes a flavin reductase.

In some embodiments, the flavonoid 3'-hydroxylase can include an N-terminal tag having the amino acid sequence of MTTASGTNADVQNGVRP (SEQ ID NO: 20). Said flavonoid 3'-hydroxylase can be the putative pyoverdine chromophore biosynthetic protein C from *Streptomyces sclerotialus* having the amino acid sequence of SEQ ID NO: 12 or a variant thereof. More specifically, the flavonoid 3'-hydroxylase can include an amino acid sequence having at least 80%, 85%, 90%, 95%, 96%, 97%, 98%, 99% sequence identity to the amino acid sequence of SEQ ID NO: 12. In some embodiments, the flavonoid 3'-hydroxylase can include an amino acid sequence having at least 80% sequence identity to the amino acid sequence of SEQ ID NO: 12 and the amino acid sequence of SEQ ID NO: 20. In certain embodiments, the flavonoid 3'-hydroxylase can include one or more mutations selected from the group consisting of M196Y. G315H, and D214N compared to the amino acid sequence of SEQ ID NO: 12. Each of these mutants can include an N-terminal tag having the amino acid sequence of MTTASGTNADVQNGVRP. In some embodiments, the flavonoid 3'-hydroxylase can comprise the amino acid sequence of SEQ ID NO: 2, SEQ ID NO: 4, SEQ ID NO: 6, SEQ ID NO: 8, or SEQ ID NO: 10. In certain embodiments, the flavonoid 3'-hydroxylase can consist of the amino acid sequence of SEQ ID NO: 2, SEQ ID NO: 4, SEQ ID NO: 6, SEQ ID NO: 8, or SEQ ID NO: 10. In some embodiments, the first polynucleotide sequence encoding the flavonoid 3'-hydroxylase can comprise a nucleic acid sequence having at least 80%, 85%, 90%, 95%, 96%, 97%, 98%, 99% sequence identity to the nucleic acid sequence of SEQ ID NO: 1, SEQ ID NO: 3, SEQ ID NO: 5, SEQ ID NO: 7, or SEQ ID NO: 9. In certain embodiments, the first polynucleotide sequence encoding the flavonoid 3'-hydroxylase can comprise the nucleic acid sequence of SEQ ID NO: 1, SEQ ID NO: 3, SEQ ID NO: 5, SEQ ID NO: 7, or SEQ ID NO: 9. In particular embodiments, the first polynucleotide sequence encoding the flavonoid 3'-hydroxylase can consist of the nucleic acid sequence of SEQ ID NO: 1, SEQ ID NO: 3, SEQ ID NO: 5, SEQ ID NO: 7, or SEQ ID NO: 9.

The flavin reductase can be a *Saccharothrix espanaensis* flavin reductase, a *Pseudomonas fluorescens* flavin reductase, or the reductase subunit of a 4-hydroxyphenylacetate 3-monooxygenase (HpaC) from *E. coli*. The flavin reductase can be a polypeptide comprising the amino acid sequence of SEQ ID NO: 14, SEQ ID NO: 16, or SEQ ID NO: 18. The second polynucleotide sequence encoding the flavin reductase can be selected from the group consisting of SEQ ID NO: 13, SEQ ID NO: 15, or SEQ ID NO: 17.

The host cell used herein can be selected from the group consisting of bacterium, yeast, and a combination thereof, or any cellular system that would allow the genetic transformation with the selected genes and thereafter the biosynthetic production of 3'-hydroxylated flavonoid (e.g., eriodictyol) from flavonoid (e.g., naringenin). In various embodiments, the host cell can be selected from the group of microbial species consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis: Aspergillus; Arthrobotlys; Brevibacteria; Microbacterium; Arthrobacter; Citrobacter; Klebsiella; Pantoea*; and *Clostridium*. In preferred embodiments, the host cell can be *E. coli*.

3'-Hydroxylated flavonoids such as eriodictyol produced according to the present teachings can be used in various food products, beverages, pharmaceutical products, and other oral consumable products, where the present 3'-hydroxylated flavonoids can reduce or mask any unpleasant, bitter, and/or astringent taste present in such products.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

DETAILED DESCRIPTION

Flavonoids

Flavonoids include various flavones and flavanones. Such flavones and flavanones can be described by the generic structure:

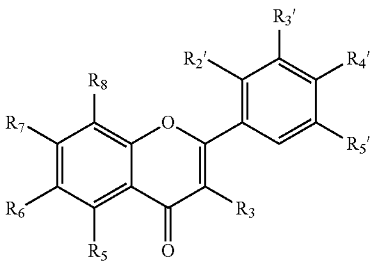

Flavone

-continued

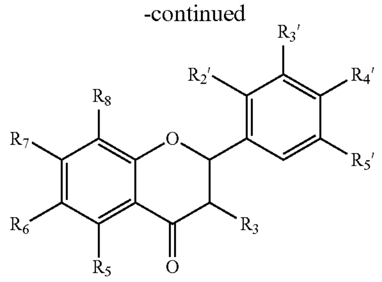

Flavanone where each of $R_{2'}$, $R_{3'}$, $R_{4'}$, $R_5$, $R_3$, $R_5$, $R_6$, $R_7$, and $R_8$ independently, can be selected from the group consisting of H, OH, and $OCH_3$. Flavonoid substrates used with the present teachings include a hydrogen atom in the $R_3$ position, while 3'-hydroxylated flavonoids produced by the present teachings include a hydroxy group in the $R_{3'}$ position. Examples of 3'-hydroxylated flavanones include eriodictyol ($R_{3'}$ is OH; $R_{4'}$, $R_5$, and $R_7$ are OH; $R_{2'}$, $R_{5'}$, $R_3$, $R_6$, and $R_8$ are H), hesperetin ($R_{3'}$ is OH; $R_{4'}$ is $OCH_3$; $R_5$, and $R_7$ are OH; $R_{2'}$, $R_{5'}$, $R_3$, $R_6$, and $R_8$ are H), and taxifolin ($R_{3'}$ is OH; $R_{4'}$, $R_3$, $R_5$, and Ry are OH; $R_{2'}$, $R_{5'}$, $R_6$, and $R_8$ are H). Examples of 3'-hydroxylated flavones include quercetin ($R_{3'}$ is OH; $R_{4'}$, $R_3$, $R_5$, and $R_7$ are OH; $R_{2'}$, $R_{5'}$, $R_6$, and $R_8$ are H), luteolin ($R_{3'}$ is OH; $R_{4'}$, $R_5$, and $R_7$ are OH; $R_{2'}$, $R_{5'}$, $R_3$, $R_6$, and $R_5$ are H), rhamnetin ($R_{3'}$ is OH; $R_{4'}$ and $R_3$ are OH; $R_7$ is $OCH_3$; $R_{2'}$, $R_{5'}$, $R_6$, and $R_8$ are H), and eupatorine ($R_{3'}$ is OH; $R_{4'}$, $R_6$ and $R_7$ are $OCH_3$; $R_5$ is OH; $R_{2'}$, $R_{5'}$, $R_3$, and $R_5$ are H).

Flavonoid 3'-Hydroxylases

The present invention provides novel flavonoid 3'-hydroxylases that are capable of converting flavonoids, such as naringenin, to 3'-hydroxylated flavonoids, such as eriodictyol, without further hydroxylating the 3'-hydroxylated flavonoids to multi-hydroxylated products.

In various embodiments, the present flavonoid 3'-hydroxylase can include an N-terminal tag having the amino acid sequence of MTTASGTNADVQNGVRP (SEQ ID NO: 20). Said flavonoid 3'-hydroxylase can be the putative pyoverdine chromophore biosynthetic protein C from *Streptomyces sclerotialus* having the amino acid sequence of SEQ ID NO: 12, or a functional homolog thereof which comprises an amino acid sequence having at least 80%, at least 85%, at least 90%, at least 95%, at least 98%, at least 99% sequence identity to the amino acid sequence of SEQ ID NO: 12. In certain embodiments, the flavonoid 3'-hydroxylase can be a mutant enzyme including one or more mutations selected from the group consisting of M196Y, G315H, and D214N compared to the amino acid sequence of SEQ ID NO: 12. Each of these mutants can include an N-terminal tag having the amino acid sequence of MTTASGTNADVQNGVRP. In some embodiments, the flavonoid 3'-hydroxylase can include the amino acid sequence of SEQ ID NO: 2, 4, 6, 8, or 10.

Flavin Reductase

Figure 1:
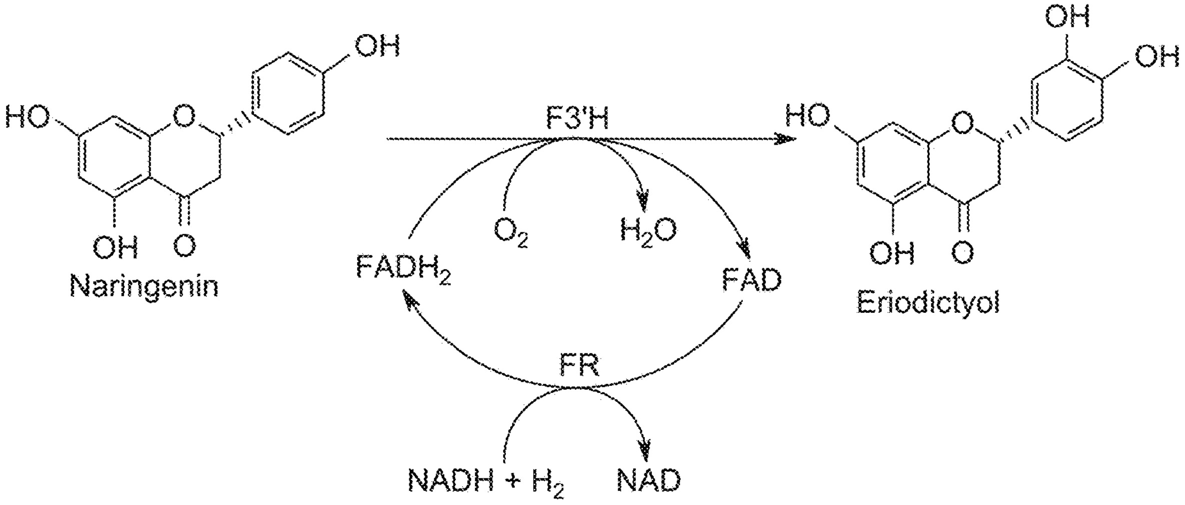
FIG. 1 illustrates how a flavonoid 3'-hydroxylase (F3'H) and a flavin reductase (FR) participate in the conversion of naringenin to eriodictyol.

Referring to FIG. 1, the bioconversion of flavonoid to 3'-hydroxylated flavonoid can be enhanced when the flavonoid 3'-hydroxylase is co-expressed with a flavin reductase. In various embodiments according to the present teachings, the flavin reductase can be a *Saccharothrix espanaensis* flavin reductase, a *Pseudomonas fluorescens* flavin reductase, or the reductase subunit of a 4-hydroxyphenylacetate 3-monooxygenase (HpaC) from *E. coli*. The flavin reductase can be a polypeptide comprising the amino acid sequence of SEQ ID NO: 14, 16, or 18.

Production Systems

Expression vectors including the present polynucleotide sequences for encoding the flavonoid 3'-hydroxylase and flavin reductase described herein can be used to transform host cells for producing 3'-hydroxylated flavonoids according to the present teachings. Other elements for the transcription and translation of the polynucleotide sequences can include a promoter, a coding region for the enzymes, and a transcriptional terminator.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR). In molecular cloning, a vector is a DNA molecule used as a vehicle to artificially carry foreign genetic material into another cell, where it can be replicated and/or expressed (e.g.—plasmid, cosmid, Lambda phages). A vector containing foreign DNA is considered recombinant DNA. The four major types of vectors are plasmids, viral vectors, cosmids, and artificial chromosomes. Of these, the most commonly used vectors are plasmids. Common to all engineered vectors are an origin of replication, a multicloning site, and a selectable marker.

A number of molecular biology techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities, thereby generating blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, Nucl. Acid. Res. 18 6069-74, (1990), Haun, et al, Biotechniques 13, 515-18 (1992), each of which are incorporated herein by reference).

In an embodiment, in order to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared using PCR appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector, In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a petunia plant cell.

In certain embodiments, the transformed host cell can be selected from the group consisting of bacterium, yeast, and a combination thereof, or any cellular system that would allow the genetic transformation with the selected genes and thereafter the biosynthetic production of 3'-hydroxylated flavonoid (e.g., eriodictyol) from flavonoid (e.g., naringenin). In various embodiments, the host cell can be selected from the group of microbial species consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis: Aspergillus; Arthrobotlys; Brevibacteria; Microbacterium; Arthrobacter; Citrobacter; Klebsiella; Pantoea*; and *Clostridium*. In preferred embodiments, the host cell can be *E. coli.*

Microbial host cell expression systems and expression vectors containing regulatory sequences that direct high-level expression of foreign proteins that are well-known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art.

Typically the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Termination control regions may also be derived from various genes native to the microbial hosts. A termination site optionally may be included for the microbial hosts described herein.

Bioconversion of Flavonoids to 3'-Hydroxylated Flavnoids

The present teachings provide methods for producing a 3'-hydroxylated flavonoid from the corresponding flavonoid, where such methods include culturing a transformed host cell in a suitable medium that includes the flavonoid. In various embodiments, the transformed host cell comprises a synthetic or recombinant nucleic acid molecule that includes a first polynucleotide sequence that encodes a flavonoid 3'-hydroxylase according to the present teachings and a second polynucleotide sequence that encodes a flavin reductase. The transformed host cell is cultured under conditions that lead to the synthesis of the flavonoid 3'-hydroxylase, which results in the flavonoid being converted to the 3'-hydroxylated flavonoid by the transformed host cell.

In various embodiments, the transformed host cell can be cultured at a temperature range of about 25° C. to about 40° C. The culture medium can include one or more amino acids, and optionally glucose and/or an antibiotic. The transformed host cell can be cultured for a sufficient period of time until stable cell growth is reached. This typically is referred to as the cell growth phase and can be between about 15 to about 18 hours. The flavonoid substrate can be added only after stable cell growth is reached, or about 15 to about 18 hours after the transformed host cell is added to the culture medium. Once the flavonoid substrate is added, the bioconversion phase begins. Such bioconversion phase can take place between about 15 to 18 hours after the transformed host cell is added to the culture medium and can last until about 40 to 60 hours after the transformed host cell is added to the culture medium.

Use of the 3'-Hydroxylated Flavonoids

3'-Hydroxylated flavonoids such as eriodictyol produced according to the present teachings can be used in various food products, beverages, pharmaceutical products, and other oral consumable products, where the present 3'-hydroxylated flavonoids can reduce or mask any unpleasant, bitter, and/or astringent taste present in such products. Such products can include one or more natural or artificial sweeteners which have a bitter aftertaste. One with skill in the art will recognize that the 3'-hydroxylated flavonoids produced by the method described herein can be further purified and mixed with other dietary supplements, medical compositions, cosmeceuticals, for nutrition, as well as in pharmaceutical products.

Molecular biology plays a pivotal role in innovating cosmoceuticals. Compound identification now begins with the identification of molecular targets. For example, the importance of free radicals in association with skin aging has led in recent years to an intensive search for active substances which eliminate the harmful effects of free radicals and thus protect the tissue from oxidative damage. Skin aging manifests as age spots, more specifically as melasma, dyschromia, melanomas, and wrinkling, mainly attributed to free radical damage to the tissues that triggers cross linking and glycation of structural proteins, and pro-inflammatory enzyme systems. The use of flavonoids in cosmetics or pharmacy is known per se. Natural antioxidants, such as the eriodictyol of the invention, that quench free radicals are an essential component of anti-ageing formulations. They potentially offer protection against damage to the tissues, and against the detrimental effects of environmental and other agents. Biochemical reactions that accelerate the progression of skin ageing have their roots in inflammatory processes, as inflammation generates micro-scars that develop into blemishes or wrinkles.

Flavonoids including flavones and flavone glycoside derivatives discussed herein are known to be scavengers of oxygen radicals and inhibitors of skin proteases so that they are actively able to counteract the aging of the skin and scar formation. By virtue of their coloring properties, some flavones, such as quercetin, are also useful as food colorants. At the same time, their ability to trap oxygen radicals also enables them to be used as antioxidants. Some flavonoids are inhibitors of aldose reductase which plays a key role in the formation of diabetes damage (ex: vascular damage). Other flavonoids (such as hesperidin and rutin) are used therapeutically, more particularly as vasodilating capillary-active agents.

Scientific research has confirmed a wide influence of flavonoid compounds on various levels of the skin. The uppermost layer of the skin, the stratum corneum, is a structure very rich in lipids and other easily oxidizable compounds. In this layer flavonoids can play an efficient role as anti-oxidizing agents and free radical scavengers. Their antioxidant properties enable them to influence deeper, epidermal skin layers, preventing UV radiation damage and inhibiting some enzyme functions. In the dermis, the deepest skin layer, flavonoids influence the permeability and fragility of the micro-vessel system. The valuable features of flavonoids described above makes them valuable for the cosmetic industry.

Definitions

"Cellular system" is any cells that provide for the expression of ectopic proteins. It included bacteria, yeast, plant cells and animal cells. It includes both prokaryotic and eukaryotic cells. It also includes the in vitro expression of proteins based on cellular components, such as ribosomes.

"Coding sequence" is to be given its ordinary and customary meaning to a person of ordinary skill in the art, and is used without limitation to refer to a DNA sequence that encodes for a specific amino acid sequence.

Growing the Cellular System. Growing includes providing an appropriate medium that would allow cells to multiply and divide. It also includes providing resources so that cells or cellular components can translate and make recombinant proteins.

Protein Expression. Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Yeast. According to the current invention a yeast as claimed herein are eukaryotic, single-celled microorganisms classified as members of the fungus kingdom. Yeasts are unicellular organisms which evolved from multicellular ancestors but with some species useful for the current invention being those that have the ability to develop multicellular characteristics by forming strings of connected budding cells known as pseudo hyphae or false hyphae.

Structural Terms:

As used herein, the singular forms "a, an" and "the" include plural references unless the content clearly dictates otherwise.

To the extent that the term "include." "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "complementary" is to be given its ordinary and customary meaning to a person of ordinary skill in the art, and is used without limitation to describe the relationship between nucleotide bases that are capable to hybridizing to one another. For example, with respect to DNA, adenosine is complementary to thymine and cytosine is complementary to guanine. Accordingly, the subjection technology also includes isolated nucleic acid fragments that are complementary to the complete sequences as reported in the accompanying Sequence Listing as well as those substantially similar nucleic acid sequences The terms "nucleic acid" and "nucleotide" are to be given their respective ordinary and customary meanings to a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein means a process of mixing two or more chemical or biological entities (such as a chemical compound and an enzyme) and allowing them to interact under conditions favorable for producing an eriodictyol composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are to be given their respective ordinary and customary meanings to a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full-length polypeptide or protein, and has substantially the same biological activity, or carries out substantially the same function as the full-length polypeptide or protein (e.g., carrying out the same enzymatic reaction).

The terms "variant polypeptide," "modified amino acid sequence" or "modified polypeptide." which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions, and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from super families and homologous polynucleotides or proteins from different species (Reeck et al., Cell 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81° C., at least 82%, at least 83%, at least 84%, at least 85%, at least 86%, at least 87%, at least 88%, at least 89%, at least 900 at least 91%, at least 92%, at least 93%, at least 94%, at least 95%, at least 96%, at least 97%, at least 98%, at least 99%, and even 100% identical.

"Suitable regulatory sequences" is to be given its ordinary and customary meaning to a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is to be given its ordinary and customary meaning to a person of ordinary skill in the art, and is used without limitation to refer to the transcription and stable accumulation of sense (mRNA) or antisense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of ordinary skill in the art, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments may be referred to as "transgenic."

The terms "transformed," "transgenic," and "recombinant," when used herein in connection with host cells, are to be given their respective ordinary and customary meanings to a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art, and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these examples, while indicating preferred embodiments of the subject technology, are given by way of illustration only. From the above discussion and these examples, one skilled in the art can ascertain the essential characteristics of the subject technology, and without departing from the spirit and scope thereof, can make various changes and modifications of the subject technology to adapt it to various uses and conditions.

Examples

Materials and Methods

Bacterial Strains, Plasmids and Culture Conditions.

*E. coli* strains of DH5a and BL21 (DE3) were purchased from Invitrogen. *E. coli* strain W3110 was obtained from the *Coli* Genetic Stock Center, *E. coli* Genetic Resources at Yale University (http://cgsc2.biology.yale.edu/). Plasmid pET21a was purchased from EMD Millipore (Billerica, MA, USA). Plasmid pUVAP was constructed by the inventors with the nucleotide sequence listed in SEQ. ID NO: 1 and the plasmid map shown in FIG. 1, which was used for both gene cloning and gene expression purposes.

DNA Manipulation.

All DNA manipulations were performed according to standard procedures.

Restriction enzymes and T4 DNA ligase were purchased from New England Biolabs. All PCR reactions were performed with New England Biolabs' Phusion PCR system according to the manufacturer's guidance.

Identification of Target Genes

SsPvcC, a putative pyoverdin chromophore biosynthetic protein C from *Streptomyces sclerotialus* with a NCBI RefSeq: WP_107054157.1, was identified in NCBI database. Its protein sequence is listed as SEQ ID NO: 10. The corresponding nucleotide sequence of its gene was synthesized by GenScript Company after codon optimization for expression in *E. coli* (SEQ ID NO: 9).

Mutation of SsPvcC by PCR

Several mutants were generated by site-directed mutagenesis. After screening a large number of mutants for the bioconversion of naringenin to eriodictyol, the inventors unexpectedly identified the mutant M196Y with significantly increased conversion activity (M196Y nucleic acid sequence-SEQ ID NO: 1, M196Y amino acid sequence-SEQ ID NO: 2) and additionally identified a 17 amino acid tag that could be introduced at the N-terminal of the SsPvcC mutant gene product to boost eriodictyol production further (M196Y+Tag nucleic acid sequence-SEQ ID NO: 3, M196Y+Tag amino acid sequence-SEQ ID NO: 4). Mutants G315H (G315H nucleic acid sequence-SEQ ID NO: 5, G315H amino acid sequence-SEQ ID NO: 6) and D214N (D214N nucleic acid sequence-SEQ ID NO: 7, D214N amino acid sequence-SEQ ID NO: 8) also were generated.

Construction of Plasmids.

The DNA fragments of SsPvcC and related mutants, respectively, were co-expressed with SeFR1, a flavin reductase. Specifically, an expression vector SsPvcC-SeFR-pRSF including 5814 base pairs (FIG. 2), harboring the genes SsPvcC (or related mutants) and SeFR1, was constructed by Gibson assembly with the plasmid of SAM5-SeFR-pRSF (see U.S. Patent Application Publication No. US 2019/0048374) as the template.

Figure 3:
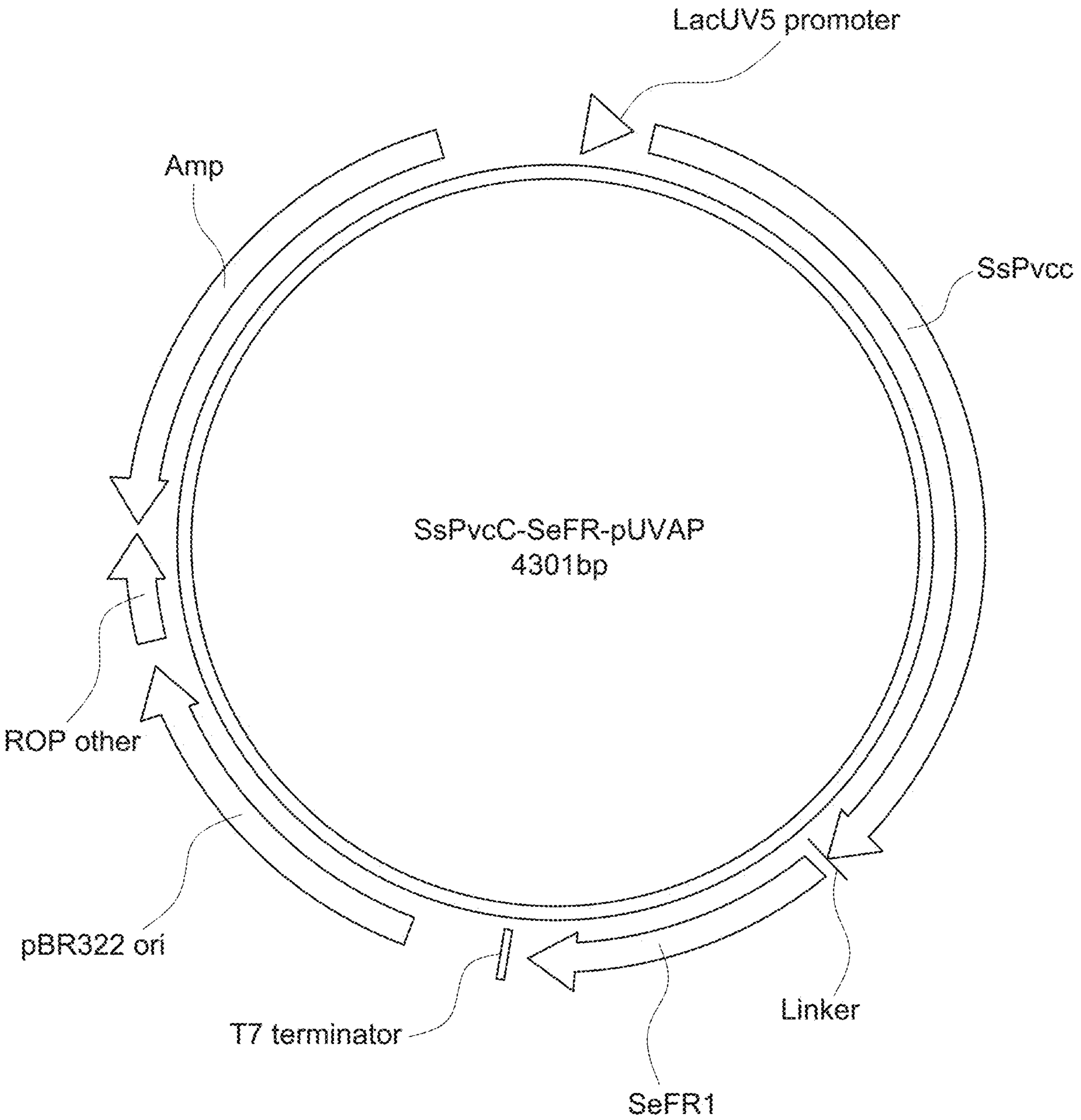
FIG. 3 shows the plasmid map of SsPvcC-SeFR-pUVAP including its key components.

Another expression vector was constructed by ligation. The DNA fragment of SsPvcC-SeFR was inserted into the Nde I and Xho I restriction sites of pUVAP, generating an expression vector SsPvcC-SeFR-pUVAP (FIG. 3).

Transformation of *E. coli* BL21 (DE3) with the Developed Constructs.

SsPvcC-SeFR-pRSF and the generated mutation variants (i.e., replacing SsPvcC with mutant M196Y and mutant M196Y-Tag, and also with mutants G315H and D214N) was introduced into *E. coli* BL21 (DE3) cells, respectively, with standard chemical transformation protocol, leading to the development of eriodictyol-producing *Escherichia coli* strains, referred herein as WT, M196Y, G315H, D214N and M196Y+Tag. Plasmid SsPvcC-SeFR-pUVAP with mutations of M196Y+Tag was introduced into *E. coli* W3110 competent cells with standard chemical transformation protocol, leading to the development of eriodictyol-producing *E. coli* strains ERI-10.

Bioconversion of Naringenin to Eriodictyol in Shaking Flasks

*Escherichia coli* BL21 (DE3) strains WT, M196Y, D315H, D214N and M196Y+Tag were grown in LB medium with 30 μg/L kanamycin. The cells were grown to $OD_{600}$ in a shaker at 37° C., and when they reached 0.6 to 0.8 the temperature was changed to 30° C. with the addition of lactose to final concentration of 1.5% (w/v) to induce the expression of exogenous genes. After 3 hours of expression induction, naringenin (40% w/v) dissolved in DMSO was added to the culture. The culture was kept shaking under the same culture condition. Samples were taken at 6 hours after substrate feeding for HPLC analysis.

Bioconversion of Naringenin to Eriodictyol in 5-Liter Fermenter

A fermentation process was developed for the bioconversion of naringenin to eriodictyol in fermenters. Glycerol stock of ERI-10 of 1 mL was inoculated into 100 mL seed culture medium (Luria-Bertani medium with 5 g/L yeast extract, 10 g/L tryptone, 10 g/L NaCl, and 50 mg/L ampicillin) in 500 mL flasks. The seed was cultivated in a shaker with the shaking speed of 200 rpm at 37° C. for 8 hours, and then transferred into 3 liter of fermentation medium of Luria-Bertani medium plus 10 g/L of initial glucose and 50 mg/L of ampicillin in a 5-liter fermenter.

The 5-liter fermenter process has two phases, cell growth phase and bioconversion phase. Cell growth phase was from elapsed fermentation time (EFT) 0 hour to about EFT 16.5 hours. The fermentation parameters were set as follows: Air flow: 0.6 vvm; pH was not below 7.1 controlled by using 4N NaOH. The growth temperature was set to 30° C. and the agitation was set to 300-500 rpm. The dissolved oxygen (DO) was cascaded to agitation to maintain above 30%. The growth time was about 16-17 hours.

Bioconversion phase was from EFT 18 hours to 48 hours. The fermentation parameters were set as follows: Air flow: 0.4 vvm. pH was controlled to not below 8.0 with 4N NaOH, and the temperature was 30° C. Agitation was set to 250-500 rpm and DO was maintained above 30% by cascaded to agitation. Naringenin dissolved in DMSO (40% volume/volume) was fed at a feeding rate of 0.15 g/L at EFT 18 hour, and then the rate was reduced to 0.1 g/L at EFT 28 hour until EFT 44 hour and the fermentation phase was completed at EFT 48 hour.

The cultural mixture was taken from the fermenter at indicated time intervals and HPLC sample was prepared as described above.

HPLC and LC-MS Analysis.

HPLC analysis of flavonoids was carried out with Dionex Ultimate 3000 system. Intermediates were separated by reverse-phase chromatography on a Dionex Acclaim 120 C18 column (particle size 3 μm; 150 by 2.1 mm) with a gradient of 0.15% (vol/vol) acetic acid (eluant A) and acetonitrile (eluant B) in a range of 10 to 40% (vol/vol) eluant B and at a flow rate of 0.6 ml/min. For quantification, all intermediates were calibrated with external standards. The compounds were identified by their retention times, as well as the corresponding spectra, which were identified with a diode array detector in the system.

Results

Figure 2:
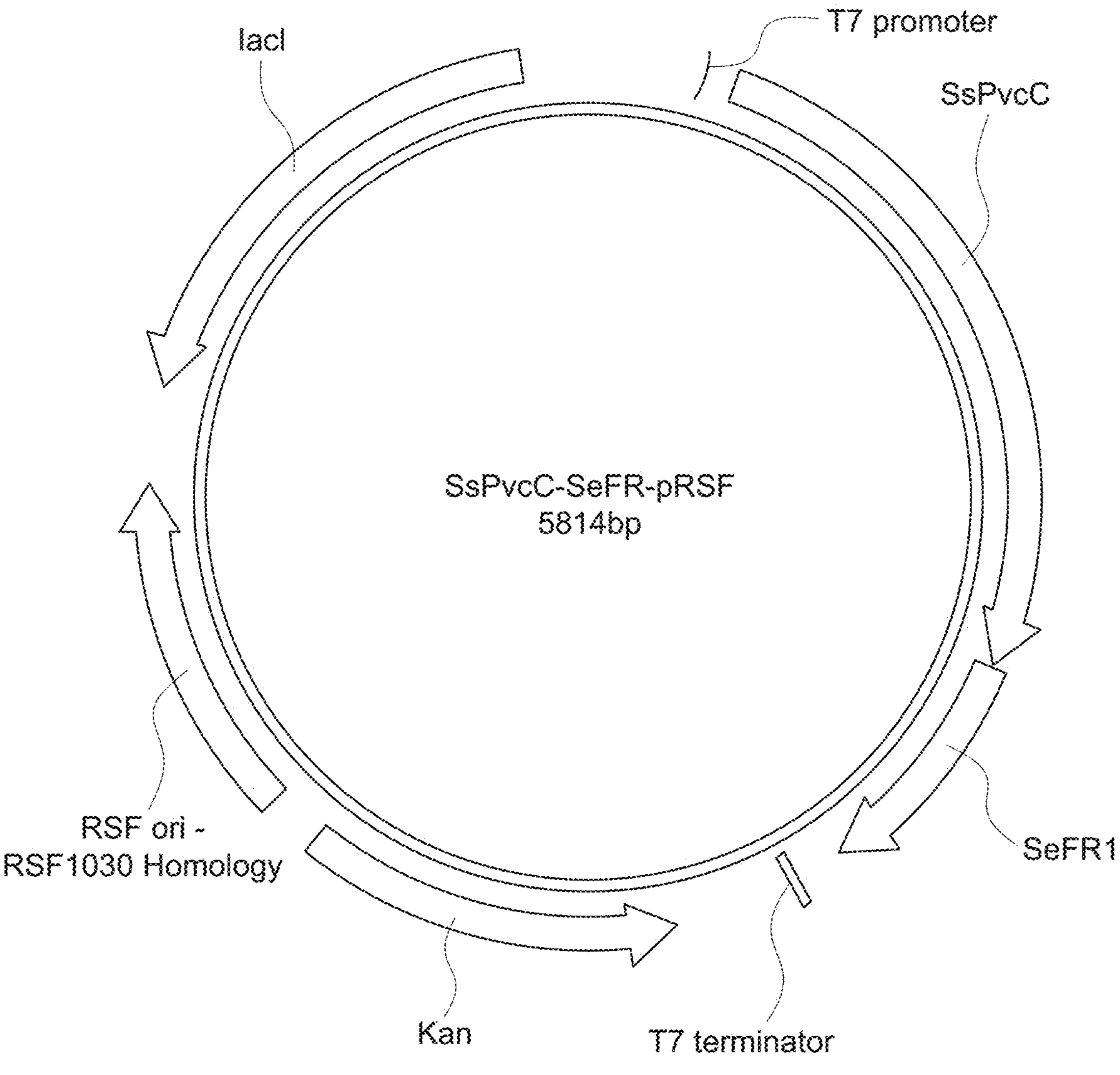
FIG. 2 shows the plasmid map of SsPvcC-SeFR-pRSF including its key components.

Wild-Type SsPvcC Showed Little Activity in the Bioconversion of Naringenin to Eriodictyol In co-owned, co-pending U.S. Patent Application Publication No. US 2019/0048374, the inventors have shown that co-expressing a flavin reductase could lead to increased bioconversion of naringenin to eriodictyol catalyzed by SAM5. Using similar strategies, the inventors constructed an expression plasmid SsPvcC-SeFR-pRSF with an expression operon of SsPvcC and SeFR1 in pRSFDuet-1 vector (FIG. 2). However, *E. coli* strain harboring wild-type SsPvcC (WT) showed very low activity in the bioconversion of naringenin to eriodictyol even when a flavin reductase, SeFR1, was co-expressed (FIG. 4).

Figure 4:
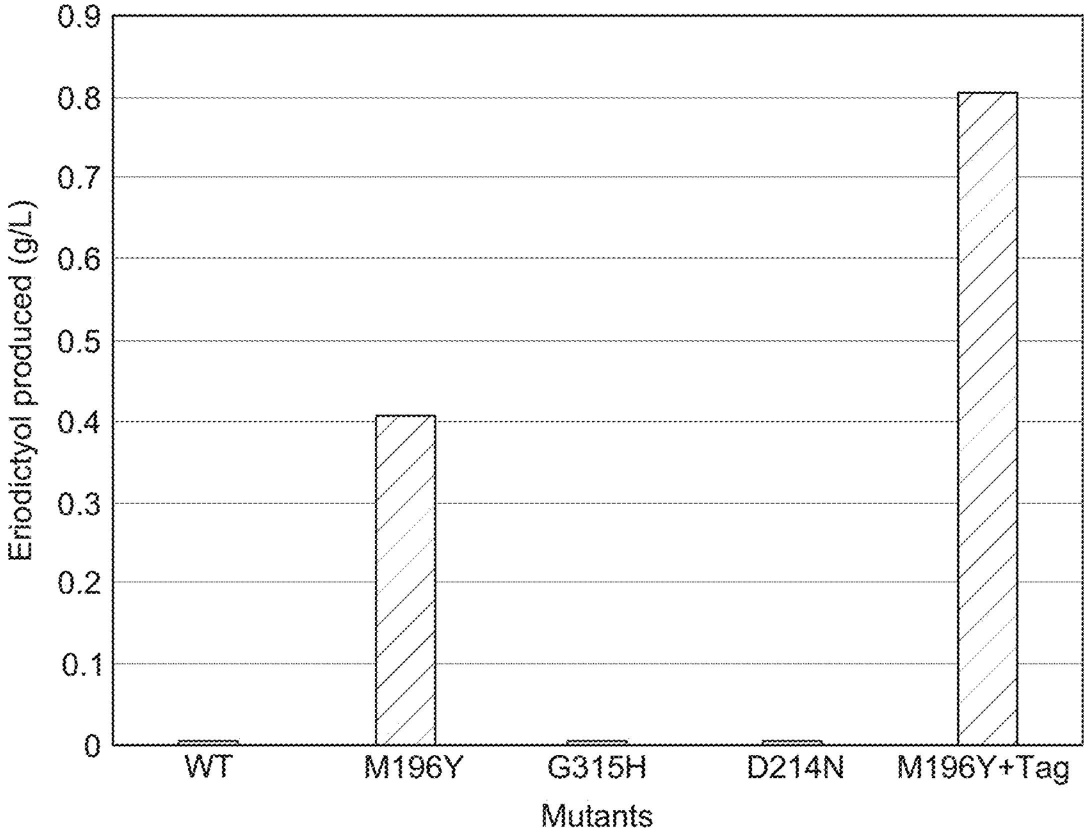
FIG. 4 compares the amount of eriodictyol produced by *E. coli* strains transformed with a *Saccharothrix espanaensis* flavin reductase (SeFR) and a flavonoid 3'-hydroxylase (F3'H), where the F3'H is either a wild-type pyoverdine chromophore protein C from *Streptomyces sclerotialus* (SsPvcC) (WT), a SsPvcC-M196Y mutant (M196Y), a SsPvcC-G315H mutant (G315H), a SsPvcC-D214N mutant (D214N), or a SsPvcC-M16Y+Tag mutant (M196Y+Tag).

Site-Directed Mutagenesis Dramatically Increased Bioconversion of Naringenin to Eriodictyol As shown in FIG. 4, specific amino acid residue mutations in SsPvcC led to dramatic increases in the bioconversion of naringenin to eriodictyol. Specifically, it was unexpectedly found that replacing methionine with tyrosine at position 196 (M196Y) led to a >100× increase in the production of eriodictyol in shaking flasks.

Furthermore, the addition of a 17-amino acid tag at the N-terminal of SsPvcC was found to further increase the titer by 98% (M196Y+Tag vs. M196Y) (FIG. 4).

Figure 5:
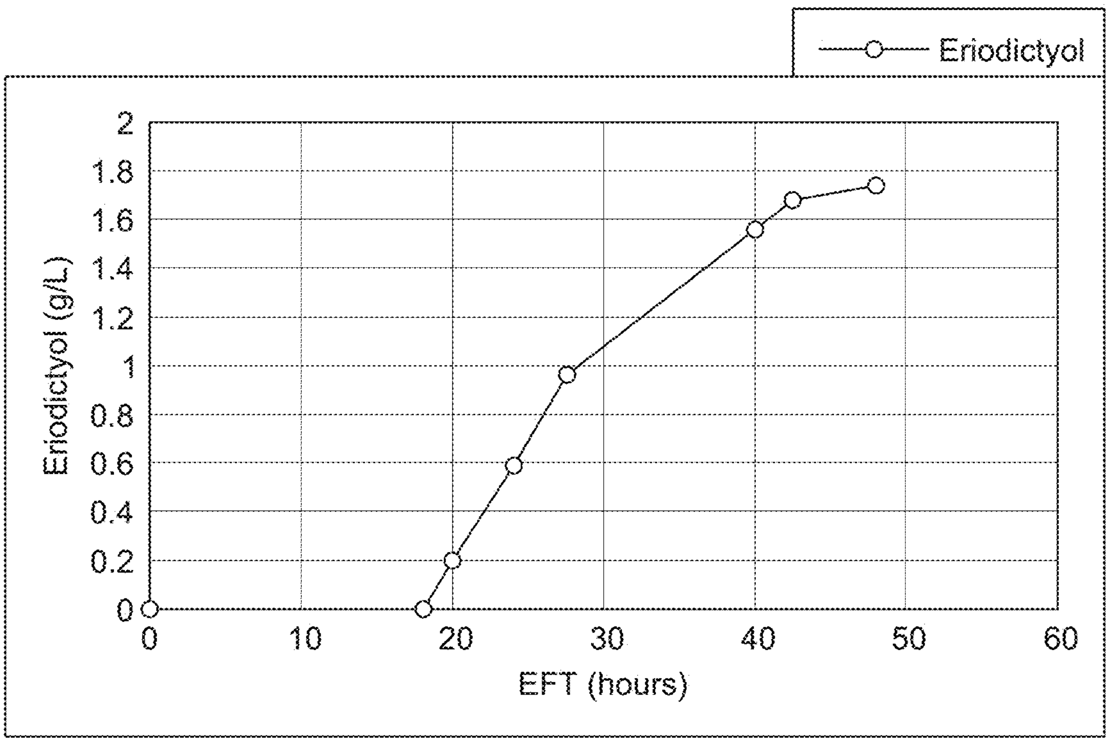
FIG. 5 shows that using an *E. coli* strain transformed with SeFR and M196Y+Tag, production of eriodictyol reached 1.74 g/L.

Thus, the inventors have developed a fermentation process using the ERI-10 strain to produce natural eriodictyol from natural naringenin, where the eriodictyol production titer reached 1.74 g/L in 48 hours (FIG. 5).

```
Sequences of Interest
Seq ID #1
SsPvcC-M196Y NT
Artificial Sequence; site-directed mutagenesis
ATGACGGGCGCCGAATATCTGGATTCGCTGCGTGA

TGGCCGTGCCGTCTATATTCACGGCGAACGCGTCC

GCGATGTCACCGCGCATCCGGCCTTCCGTAACAGC

GCGCGTAGTCTGGCGCAGCTGTATGATGTGCTGCA

TGAACCGGATTCGCGTGGCGTTCTGAGCGTCCCGA

CCGATACCGGTAATGGCGGTTTTACGCACCCGTTT

TTCAAAACCGCGCGTAGCGCCGGTGATCTGGTGGC

AGCCCGCGATGCAATTGTGGCCTGGCAGCGTCTTG

TTTACGGTTGGATGGGTCGTACGCCGGATTATAAA

GCAGCATTCTTCGGTACGCTTGAAGCCAACGCCGA

TTTCTATGGCCCGTTCCGTGATAACGCACTGGCAT

GGTATCGTCGTGCACAGGAACGCGTGTTGTATTTC

AACCATGCGATCGTGCATCCGCCGGTCGATCGCGA

TCGCCCGGCCGATCGCACGGCGGATGTGTGCGTCC

ACGTGGAAGAAGAAACGGATGCCGGCCTTGTTGTT

TCGGGTGCGAAAGTTGTCGCGACCAGCAGCGCCCT

GACGAATGCCAATCTGATTGCACACTACGGCTTAC

CGCTGCGTGATAAACGCTTTGGCGCCATGTTCACC

GTGCCGATGGATAGCCCGGGCCTGAAACTGTTCTG

TCGTACCAGTTATGAAATGCATGCCGCGGTCTTAG

GCTCGCCGTTTGATTACCCGTTAAGCAGCCGCCTT

GATGAAAATGATTCAATCATGGTTCTTGATCGTGT

TTTAGTGCCGTGGGAAAACGTGTTTATGTATGATG

CCGCCAGCGCGAACGCGTTTGCGACCCGCAGCGGT

TTCCTGGAACGTTTTACCTTTCATGGCTGTACGCG

CTTAGCGGTGAAACTGGATTTTATTGCCGGTTGCC

TGCTGAAAGCAGTTGAAGTGACCGGCACCAGCGGC

TTCCGTGGTGTGCAGGCCCAGATTGGCGAAGTTTT

AAACTGGCGCGATATGTTTTGGGGTATGTCAGATG

CAATGGCGAAATCGCCGACGGATTGGCACAATGGT

GCGGTCCAGCCGAATCTGAACTATGGCCTGGCCTA

CCGCACCTTCATGGGCATTGGTTACCCGCGTATCC

GTGAAATCATTCAGCAGACCATTGGCTCGGGTCTG

ATTTATTTAAATAGTCACGCAAGCGATTGGAAAAA

TCCGGAAGTTCGTCCGTACTTAGATCGCTACCTGC

GCGGTAGTCGTGGTGTTGAAGCGATCGATCGCGTT
```

-continued

AAACTGCTTAAACTGCTGTGGGATTGCGTGGGCAC

GGAATTTGCGGGCCGTCACGAACTTTATGAACGCA

ATTACGGTGGCGATCATGAAGGTATTCGCGTGCAG

ACCCTGTTGAGTTATCAGGCGCGCGGTCAGGCGGA

TGCGCTTAAAGGCTTTGCCGATCAGTGTATGTCAG

AATACGATCTGGATGGCTGGACCCGCCCGGATTTA

TTCGGTCCAGGTGATTTACCTAGACCAGCTACTGG

AGCGTAA

Seq ID #2
SsPvcC-M196Y AA
Artificial Sequence; site-directed mutagenesis
MTGAEYLDSLRDGRAVYIHGERVRDVTAHPAFRNS

ARSLAQLYDVLHEPDSRGVLSVPTDTGNGGFTHPF

FKTARSAGDLVAARDAIVAWQRLVYGWMGRTPDYK

AAFFGTLEANADFYGPFRDNALAWYRRAQERVLYF

NHAIVHPPVDRDRPADRTADVCVHVEEETDAGLVV

SGAKVVATSSALTNANLIAHYGLPLRDKRFGAMFT

VPMDSPGLKLFCRTSYEMHAAVLGSPFDYPLSSRL

DENDSIMVLDRVLVPWENVFMYDAASANAFATRSG

FLERFTFHGCTRLAVKLDFIAGCLLKAVEVTGTSG

FRGVQAQIGEVLNWRDMFWGMSDAMAKSPTDWHNG

AVQPNLNYGLAYRTFMGIGYPRIREIIQQTIGSGL

IYLNSHASDWKNPEVRPYLDRYLRGSRGVEAIDRV

KLLKLLWDCVGTEFAGRHELYERNYGGDHEGIRVQ

TLLSYQARGQADALKGFADQCMSEYDLDGWTRPDL

FGPGDLPRPATGA

Seq ID #3 SsPvcC-M196Y-Tag NT
Artificial Sequence; N-terminal tag and site-directed mutagenesis
ATGACGACCGCTAGTGGTACCAATGCAGATGTCCA

GAATGGCGTCCGCCCGATGACGGGCGCCGAATATC

TGGATTCGCTGCGTGATGGCCGTGCCGTCTATATT

CACGGCGAACGCGTCCGCGATGTCACCGCGCATCC

GGCCTTCCGTAACAGCGCGCGTAGTCTGGCGCAGC

TGTATGATGTGCTGCATGAACCGGATTCGCGTGGC

GTTCTGAGCGTCCCGACCGATACCGGTAATGGCGG

TTTTACGCACCCGTTTTTCAAAACCGCGCGTAGCG

CCGGTGATCTGGTGGCAGCCCGCGATGCAATTGTG

GCCTGGCAGCGTCTTGTTTACGGTTGGATGGGTCG

TACGCCGGATTATAAAGCAGCATTCTTCGGTACGC

TTGAAGCCAACGCCGATTTCTATGGCCCGTTCCGT

GATAACGCACTGGCATGGTATCGTCGTGCACAGGA

ACGCGTGTTGTATTTCAACCATGCGATCGTGCATC

-continued

CGCCGGTCGATCGCGATCGCCCGGCCGATCGCACG

GCGGATGTGTGCGTCCACGTGGAAGAAGAAACGGA

TGCCGGCCTTGTTGTTTCGGGTGCGAAAGTTGTCG

CGACCAGCAGCGCCCTGACGAATGCCAATCTGATT

GCACACTACGGCTTACCGCTGCGTGATAAACGCTT

TGGCGCCATGTTCACCGTGCCGATGGATAGCCCGG

GCCTGAAACTGTTCTGTCGTACCAGTTATGAAATG

CATGCCGCGGTCTTAGGCTCGCCGTTTGATTACCC

GTTAAGCAGCCGCCTTGATGAAAATGATTCAATCA

TGGTTCTTGATCGTGTTTTAGTGCCGTGGGAAAAC

GTGTTTATGTATGATGCCGCCAGCGCGAACGCGTT

TGCGACCCGCAGCGGTTTCCTGGAACGTTTTACCT

TTCATGGCTGTACGCGCTTAGCGGTGAAACTGGAT

TTTATTGCCGGTTGCCTGCTGAAAGCAGTTGAAGT

GACCGGCACCAGCGGCTTCCGTGGTGTGCAGGCCC

AGATTGGCGAAGTTTTAAACTGGCGCGATATGTTT

TGGGGTATGTCAGATGCAATGGCGAAATCGCCCGAC

GGATTGGCACAATGGTGCGGTCCAGCCGAATCTGA

ACTATGGCCTGGCCTACCGCACCTTCATGGGCATT

GGTTACCCGCGTATCCGTGAAATCATTCAGCAGAC

CATTGGCTCGGGTCTGATTTATTTAAATAGTCACG

CAAGCGATTGGAAAAATCCGGAAGTTCGTCCGTAC

TTAGATCGCTACCTGCGCGGTAGTCGTGGTGTTGA

AGCGATCGATCGCGTTAAACTGCTTAAACTGCTGT

GGGATTGCGTGGGCACGGAATTTGCGGGCCGTCAC

GAACTTTATGAACGCAATTACGGTGGCGATCATGA

AGGTATTCGCGTGCAGACCCTGTTGAGTTATCAGG

CGCGCGGTCAGGCGGATGCGCTTAAAGGCTTTGCC

GATCAGTGTATGTCAGAATACGATCTGGATGGCTG

GACCCGCCCGGATTTATTCGGTCCAGGTGATTTAC

CTAGACCAGCTACTGGAGCGTAA

Seq ID #4
SsPvcC-M196Y-Tag AA
Artificial Sequence; N-terminal tag and site-directed mutagenesis
MTTASGTNADVQNGVRPMTGAEYLDSLRDGRAVYI

HGERVRDVTAHPAFRNSARSLAQLYDVLHEPDSRG

VLSVPTDTGNGGFTHPFFKTARSAGDLVAARDAIV

AWQRLVYGWMGRTPDYKAAFFGTLEANADFYGPFR

DNALAWYRRAQERVLYFNHAIVHPPVDRDRPADRT

ADVCVHVEEETDAGLVVSGAKVVATSSALTNANLI

AHYGLPLRDKRFGAMFTVPMDSPGLKLFCRTSYEM

-continued

HAAVLGSPFDYPLSSRLDENDSIMVLDRVLVPWEN

VFMYDAASANAFATRSGFLERFTFHGCTRLAVKLD

FIAGCLLKAVEVTGTSGFRGVQAQIGEVLNWRDMF

WGMSDAMAKSPTDWHNGAVQPNLNYGLAYRTFMGI

GYPRIREIIQQTIGSGLIYLNSHASDWKNPEVRPY

LDRYLRGSRGVEAIDRVKLLKLLWDCVGTEFAGRH

ELYERNYGGDHEGIRVQTLLSYQARGQADALKGFA

DQCMSEYDLDGWTRPDLFGPGDLPRPATGA

Seq ID #5
SsPvcC-G315H + Tag NT
Artificial Sequence; N-terminal tag + Site-Directed Mutagenesis
ATGACGACCGCTAGTGGTACCAATGCAGATGTCCA

GAATGGCGTCCGCCCGATGACGGGCGCCGAATATC

TGGATTCGCTGCGTGATGGCCGTGCCGTCTATATT

CACGGCGAACGCGTCCGCGATGTCACCGCGCATCC

GGCCTTCCGTAACAGCGCGCGTAGTCTGGCGCAGC

TGTATGATGTGCTGCATGAACCGGATTCGCGTGGC

GTTCTGAGCGTCCCGACCGATACCGGTAATGGCGG

TTTTACGCACCCGTTTTTCAAAACCGCGCGTAGCG

CCGGTGATCTGGTGGCAGCCCGCGATGCAATTGTG

GCCTGGCAGCGTCTTGTTTACGGTTGGATGGGTCG

TACGCCGGATTATAAAGCAGCATTCTTCGGTACGC

TTGAAGCCAACGCCGATTTCTATGGCCCGTTCCGT

GATAACGCACTGGCATGGTATCGTCGTGCACAGGA

ACGCGTGTTGTATTTCAACCATGCGATCGTGCATC

CGCCGGTCGATCGCGATCGCCCGGCCGATCGCACG

GCGGATGTGTGCGTCCACGTGGAAGAAGAAACGGA

TGCCGGCCTTGTTGTTTCGGGTGCGAAAGTTGTCG

CGACCAGCAGCGCCCTGACGAATGCCAATCTGATT

GCACACATGGGCTTACCGCTGCGTGATAAACGCTT

TGGCGCCATGTTCACCGTGCCGATGGATAGCCCGG

GCCTGAAACTGTTCTGTCGTACCAGTTATGAAATG

CATGCCGCGGTCTTAGGCTCGCCGTTTGATTACCC

GTTAAGCAGCCGCCTTGATGAAAATGATTCAATCA

TGGTTCTTGATCGTGTTTTAGTGCCGTGGGAAAAC

GTGTTTATGTATGATGCCGCCAGCGCGAACGCGTT

TGCGACCCGCAGCGGTTTCCTGGAACGTTTTACCT

TTCATGGCTGTACGCGCTTAGCGGTGAAACTGGAT

TTTATTGCCGGTTGCCTGCTGAAAGCAGTTGAAGT

GACCGGCACCAGCCACTTCCGTGGTGTGCAGGCCC

AGATTGGCGAAGTTTTAAACTGGCGCGATATGTTT

TGGGGTATGTCAGATGCAATGGCGAAATCGCCGAC

-continued

GGATTGGCACAATGGTGCGGTCCAGCCGAATCTGA

ACTATGGCCTGGCCTACCGCACCTTCATGGGCATT

GGTTACCCGCGTATCCGTGAAATCATTCAGCAGAC

CATTGGCTCGGGTCTGATTTATTTAAATAGTCACG

CAAGCGATTGGAAAAATCCGGAAGTTCGTCCGTAC

TTAGATCGCTACCTGCGCGGTAGTCGTGGTGTTGA

AGCGATCGATCGCGTTAAACTGCTTAAACTGCTGT

GGGATTGCGTGGGCACGGAATTTGCGGGCCGTCAC

GAACTTTATGAACGCAATTACGGTGGCGATCATGA

AGGTATTCGCGTGCAGACCCTGTTGAGTTATCAGG

CGCGCGGTCAGGCGGATGCGCTTAAAGGCTTTGCC

GATCAGTGTATGTCAGAATACGATCTGGATGGCTG

GACCCGCCCGGATTTATTCGGTCCAGGTGATTTAC

CTAGACCAGCTACTGGAGCGTAA

Seq ID #6
SsPvcC-G315H + Tag AA
Artificial Sequence; N-terminal tag + Site-Directed Mutagenesis
MTTASGTNADVQNGVRPMTGAEYLDSLRDGRAVYI

HGERVRDVTAHPAFRNSARSLAQLYDVLHEPDSRG

VLSVPTDTGNGGFTHPFFKTARSAGDLVAARDAIV

AWQRLVYGWMGRTPDYKAAFFGTLEANADFYGPFR

DNALAWYRRAQERVLYFNHAIVHPPVDRDRPADRT

ADVCVHVEEETDAGLVVSGAKVVATSSALTNANLI

AHMGLPLRDKRFGAMFTVPMDSPGLKLFCRTSYEM

HAAVLGSPFDYPLSSRLDENDSIMVLDRVLVPWEN

VFMYDAASANAFATRSGFLERFTFHGCTRLAVKLD

FIAGCLLKAVEVTGTSHFRGVQAQIGEVLNWRDMF

WGMSDAMAKSPTDWHNGAVQPNLNYGLAYRTFMGI

GYPRIREIIQQTIGSGLIYLNSHASDWKNPEVRPY

LDRYLRGSRGVEAIDRVKLLKLLWDCVGTEFAGRH

ELYERNYGGDHEGIRVQTLLSYQARGQADALKGFA

DQCMSEYDLDGWTRPDLFGPGDLPRPATGA

Seq ID #7
SsPvcC-D214N + Tag NT
Artificial Sequence; N-terminal tag + Site-Directed Mutagenesis
ATGACGACCGCTAGTGGTACCAATGCAGATGTCCA

GAATGGCGTCCGCCCGATGACGGGCGCCGAATATC

TGGATTCGCTGCGTGATGGCCGTGCCGTCTATATT

CACGGCGAACGCGTCCGCGATGTCACCGCGCATCC

GGCCTTCCGTAACAGCGCGCGTAGTCTGGCGCAGC

TGTATGATGTGCTGCATGAACCGGATTCGCGTGGC

GTTCTGAGCGTCCCGACCGATACCGGTAATGGCGG

-continued

TTTTACGCACCCGTTTTTCAAAACCGCGCGTAGCG

CCGGTGATCTGGTGGCAGCCCGCGATGCAATTGTG

GCCTGGCAGCGTCTTGTTTACGGTTGGATGGGTCG

TACGCCGGATTATAAAGCAGCATTCTTCGGTACGC

TTGAAGCCAACGCCGATTTCTATGGCCCGTTCCGT

GATAACGCACTGGCATGGTATCGTCGTGCACAGGA

ACGCGTGTTGTATTTCAACCATGCGATCGTGCATC

CGCCGGTCGATCGCGATCGCCCGGCCGATCGCACG

GCGGATGTGTGCGTCCACGTGGAAGAAGAAACGGA

TGCCGGCCTTGTTGTTTCGGGTGCGAAAGTTGTCG

CGACCAGCAGCGCCCTGACGAATGCCAATCTGATT

GCACACATGGGCTTACCGCTGCGTGATAAACGCTT

TGGCGCCATGTTCACCGTGCCGATGAATAGCCCGG

GCCTGAAACTGTTCTGTCGTACCAGTTATGAAATG

CATGCCGCGGTCTTAGGCTCGCCGTTTGATTACCC

GTTAAGCAGCCGCCTTGATGAAAATGATTCAATCA

TGGTTCTTGATCGTGTTTTAGTGCCGTGGGAAAAC

GTGTTTATGTATGATGCCGCCAGCGCGAACGCGTT

TGCGACCCGCAGCGGTTTCCTGGAACGTTTTACCT

TTCATGGCTGTACGCGCTTAGCGGTGAAACTGGAT

TTTATTGCCGGTTGCCTGCTGAAAGCAGTTGAAGT

GACCGGCACCAGCCATTTCCGTGGTGTGCAGGCCC

AGATTGGCGAAGTTTTAAACTGGCGCGATATGTTT

TGGGGTATGTCAGATGCAATGGCGAAATCGCCGAC

GGATTGGCACAATGGTGCGGTCCAGCCGAATCTGA

ACTATGGCCTGGCCTACCGCACCTTCATGGGCATT

GGTTACCCGCGTATCCGTGAAATCATTCAGCAGAC

CATTGGCTCGGGTCTGATTTATTTAAATAGTCACG

CAAGCGATTGGAAAAATCCGGAAGTTCGTCCGTAC

TTAGATCGCTACCTGCGCGGTAGTCGTGGTGTTGA

AGCGATCGATCGCGTTAAACTGCTTAAACTGCTGT

GGGATTGCGTGGGCACGGAATTTGCGGGCCGTCAC

GAACTTTATGAACGCAATTACGGTGGCGATCATGA

AGGTATTCGCGTGCAGACCCTGTTGAGTTATCAGG

CGCGCGGTCAGGCGGATGCGCTTAAAGGCTTTGCC

GATCAGTGTATGTCAGAATACGATCTGGATGGCTG

GACCCGCCCGGATTTATTCGGTCCAGGTGATTTAC

CTAGACCAGCTACTGGAGCGTAA

-continued

Seq ID #8
SsPvcC-D214N + Tag AA
Artificial Sequence; N-terminal tag + Site-Directed Mutagenesis
MTTASGTNADVQNGVRPMTGAEYLDSLRDGRAVYI

HGERVRDVTAHPAFRNSARSLAQLYDVLHEPDSRG

VLSVPTDTGNGGFTHPFFKTARSAGDLVAARDAIV

AWQRLVYGWMGRTPDYKAAFFGTLEANADFYGPFR

DNALAWYRRAQERVLYFNHAIVHPPVDRDRPADRT

ADVCVHVEEETDAGLVVSGAKVVATSSALTNANLI

AHMGLPLRDKRFGAMFTVPMNSPGLKLFCRTSYEM

HAAVLGSPFDYPLSSRLDENDSIMVLDRVLVPWEN

VFMYDAASANAFATRSGFLERFTFHGCTRLAVKLD

FIAGCLLKAVEVTGTSGFRGVQAQIGEVLNWRDMF

WGMSDAMAKSPTDWHNGAVQPNLNYGLAYRTFMGI

GYPRIREIIQQTIGSGLIYLNSHASDWKNPEVRPY

LDRYLRGSRGVEAIDRVKLLKLLWDCVGTEFAGRH

ELYERNYGGDHEGIRVQTLLSYQARGQADALKGFA

DQCMSEYDLDGWTRPDLFGPGDLPRPATGA

Seq ID #9
SsPvcC + Tag NT
Artificial Sequence; N-terminal tag
ATGACGACCGCTAGTGGTACCAATGCAGATGTCCA

GAATGGCGTCCGCCCGATGACGGGCGCCGAATATC

TGGATTCGCTGCGTGATGGCCGTGCCGTCTATATT

CACGGCGAACGCGTCCGCGATGTCACCGCGCATCC

GGCCTTCCGTAACAGCGCGCGTAGTCTGGCGCAGC

TGTATGATGTGCTGCATGAACCGGATTCGCGTGGC

GTTCTGAGCGTCCCGACCGATACCGGTAATGGCGG

TTTTACGCACCCGTTTTTCAAAACCGCGCGTAGCG

CCGGTGATCTGGTGGCAGCCCGCGATGCAATTGTG

GCCTGGCAGCGTCTTGTTTACGGTTGGATGGGTCG

TACGCCGGATTATAAAGCAGCATTCTTCGGTACGC

TTGAAGCCAACGCCGATTTCTATGGCCCGTTCCGT

GATAACGCACTGGCATGGTATCGTCGTGCACAGGA

ACGCGTGTTGTATTTCAACCATGCGATCGTGCATC

CGCCGGTCGATCGCGATCGCCCGGCCGATCGCACG

GCGGATGTGTGCGTCCACGTGGAAGAAGAAACGGA

TGCCGGCCTTGTTGTTTCGGGTGCGAAAGTTGTCG

CGACCAGCAGCGCCCTGACGAATGCCAATCTGATT

GCACACATGGGCTTACCGCTGCGTGATAAACGCTT

TGGCGCCATGTTCACCGTGCCGATGGATAGCCCGG

GCCTGAAACTGTTCTGTCGTACCAGTTATGAAATG

CATGCCGCGGTCTTAGGCTCGCCGTTTGATTACCC

-continued

GTTAAGCAGCCGCCTTGATGAAAATGATTCAATCA

TGGTTCTTGATCGTGTTTTAGTGCCGTGGGAAAAC

GTGTTTATGTATGATGCCGCCAGCGCGAACGCGTT

TGCGACCCGCAGCGGTTTCCTGGAACGTTTTACCT

TTCATGGCTGTACGCGCTTAGCGGTGAAACTGGAT

TTTATTGCCGGTTGCCTGCTGAAAGCAGTTGAAGT

GACCGGCACCAGCGGCTTCCGTGGTGTGCAGGCCC

AGATTGGCGAAGTTTTAAACTGGCGCGATATGTTT

TGGGGTATGTCAGATGCAATGGCGAAATCGCCGAC

GGATTGGCACAATGGTGCGGTCCAGCCGAATCTGA

ACTATGGCCTGGCCTACCGCACCTTCATGGGCATT

GGTTACCCGCGTATCCGTGAAATCATTCAGCAGAC

CATTGGCTCGGGTCTGATTTATTTAAATAGTCACG

CAAGCGATTGGAAAAATCCGGAAGTTCGTCCGTAC

TTAGATCGCTACCTGCGCGGTAGTCGTGGTGTTGA

AGCGATCGATCGCGTTAAACTGCTTAAACTGCTGT

GGGATTGCGTGGGCACGGAATTTGCGGGCCGTCAC

GAACTTTATGAACGCAATTACGGTGGCGATCATGA

AGGTATTCGCGTGCAGACCCTGTTGAGTTATCAGG

CGCGCGGTCAGGCGGATGCGCTTAAAGGCTTTGCC

GATCAGTGTATGTCAGAATACGATCTGGATGGCTG

GACCCGCCCGGATTTATTCGGTCCAGGTGATTTAC

CTAGACCAGCTACTGGAGCGTAA

Seq ID #10
SsPvcC + Tag AA
Artificial Sequence; N-terminal tag
MTTASGTNADVQNGVRPMTGAEYLDSLRDGRAVYI

HGERVRDVTAHPAFRNSARSLAQLYDVLHEPDSRG

VLSVPTDTGNGGFTHPFFKTARSAGDLVAARDAIV

AWQRLVYGWMGRTPDYKAAFFGTLEANADFYGPFR

DNALAWYRRAQERVLYFNHAIVHPPVDRDRPADRT

ADVCVHVEEETDAGLVVSGAKVVATSSALTNANLI

AHMGLPLRDKRFGAMFTVPMDSPGLKLFCRTSYEM

HAAVLGSPFDYPLSSRLDENDSIMVLDRVLVPWEN

VFMYDAASANAFATRSGFLERFTFHGCTRLAVKLD

FIAGCLLKAVEVTGTSGFRGVQAQIGEVLNWRDMF

WGMSDAMAKSPTDWHNGAVQPNLNYGLAYRTFMGI

GYPRIREIIQQTIGSGLIYLNSHASDWKNPEVRPY

LDRYLRGSRGVEAIDRVKLLKLLWDCVGTEFAGRH

ELYERNYGGDHEGIRVQTLLSYQARGQADALKGFA

DQCMSEYDLDGWTRPDLFGPGDLPRPATGA

-continued

Seq ID #11:
SsPvc NT
Organism: *Streptomyces sclerotialus*
ATGACGGGCGCCGAATATCTGGATTCGCTGCGTGA

TGGCCGTGCCGTCTATATTCACGGCGAACGCGTCC

GCGATGTCACCGCGCATCCGGCCTTCCGTAACAGC

GCGCGTAGTCTGGCGCAGCTGTATGATGTGCTGCA

TGAACCGGATTCGCGTGGCGTTCTGAGCGTCCCGA

CCGATACCGGTAATGGCGGTTTTACGCACCCGTTT

TTCAAAACCGCGCGTAGCGCCGGTGATCTGGTGGC

AGCCCGCGATGCAATTGTGGCCTGGCAGCGTCTTG

TTTACGGTTGGATGGGTCGTACGCCGGATTATAAA

GCAGCATTCTTCGGTACGCTTGAAGCCAACGCCGA

TTTCTATGGCCCGTTCCGTGATAACGCACTGGCAT

GGTATCGTCGTGCACAGGAACGCGTGTTGTATTTC

AACCATGCGATCGTGCATCCGCCGGTCGATCGCGA

TCGCCCGGCCGATCGCACGGCGGATGTGTGCGTCC

ACGTGGAAGAAGAAACGGATGCCGGCCTTGTTGTT

TCGGGTGCGAAAGTTGTCGCGACCAGCAGCGCCCT

GACGAATGCCAATCTGATTGCACACATGGGCTTAC

CGCTGCGTGATAAACGCTTTGGCGCCATGTTCACC

GTGCCGATGGATAGCCCGGGCCTGAAACTGTTCTG

TCGTACCAGTTATGAAATGCATGCCGCGGTCTTAG

GCTCGCCGTTTGATTACCCGTTAAGCAGCCGCCTT

GATGAAAATGATTCAATCATGGTTCTTGATCGTGT

TTTAGTGCCGTGGGAAAACGTGTTTATGTATGATG

CCGCCAGCGCGAACGCGTTTGCGACCCGCAGCGGT

TTCCTGGAACGTTTTACCTTTCATGGCTGTACGCG

CTTAGCGGTGAAACTGGATTTTATTGCCGGTTGCC

TGCTGAAAGCAGTTGAAGTGACCGGCACCAGCGGC

TTCCGTGGTGTGCAGGCCCAGATTGGCGAAGTTTT

AAACTGGCGCGATATGTTTTGGGGTATGTCAGATG

CAATGGCGAAATCGCCGACGGATTGGCACAATGGT

GCGGTCCAGCCGAATCTGAACTATGGCCTGGCCTA

CCGCACCTTCATGGGCATTGGTTACCCGCGTATCC

GTGAAATCATTCAGCAGACCATTGGCTCGGGTCTG

ATTTATTTAAATAGTCACGCAAGCGATTGGAAAAA

TCCGGAAGTTCGTCCGTACTTAGATCGCTACCTGC

GCGGTAGTCGTGGTGTTGAAGCGATCGATCGCGTT

AAACTGCTTAAACTGCTGTGGGATTGCGTGGGCAC

GGAATTTGCGGGCCGTCACGAACTTTATGAACGCA

ATTACGGTGGCGATCATGAAGGTATTCGCGTGCAG

-continued

ACCCTGTTGAGTTATCAGGCGCGCGGTCAGGCGGA

TGCGCTTAAAGGCTTTGCCGATCAGTGTATGTCAG

AATACGATCTGGATGGCTGGACCCGCCCGGATTTA

TTCGGTCCAGGTGATTTACCTAGACCAGCTACTGG

AGCGTAA

Seq ID #12
SsPvcC AA
Organism: *Streptomyces sclerotialus*
MTGAEYLDSLRDGRAVYIHGERVRDVTAHPAFRNS

ARSLAQLYDVLHEPDSRGVLSVPTDTGNGGFTHPF

FKTARSAGDLVAARDAIVAWQRLVYGWMGRTPDYK

AAFFGTLEANADFYGPFRDNALAWYRRAQERVLYF

NHAIVHPPVDRDRPADRTADVCVHVEEETDAGLVV

SGAKVVATSSALTNANLIAHMGLPLRDKRFGAMFT

VPMDSPGLKLFCRTSYEMHAAVLGSPFDYPLSSRL

DENDSIMVLDRVLVPWENVFMYDAASANAFATRSG

FLERFTFHGCTRLAVKLDFIAGCLLKAVEVTGTSG

FRGVQAQIGEVLNWRDMFWGMSDAMAKSPTDWHNG

AVQPNLNYGLAYRTFMGIGYPRIREIIQQTIGSGL

IYLNSHASDWKNPEVRPYLDRYLRGSRGVEAIDRV

KLLKLLWDCVGTEFAGRHELYERNYGGDHEGIRVQ

TLLSYQARGQADALKGFADQCMSEYDLDGWTRPDL

FGPGDLPRPATGA

Seq ID #13:
SeFR NT
Organism: *Saccharothrix espanaensis*
ATGATGACCGTTTATGATAGCGCACTGACAATGGA

AGAAACCACCCTGCGTGATGCAATGAGCCGTTTTG

CAACCGGTGTTAGCGTTGTTACCGTTGGTGGTGAA

CATACACATGGTATGACCGCAAATGCCTTTACCTG

TGTTAGCCTGGATCCGCCTCTGGTTCTGTGTTGTG

TTGCACGTAAAGCAACCATGCATGCAGCAATTGAA

GGTGCACGTCGTTTTGCAGTTAGCGTTATGGGTGG

TGATCAAGAACGTACCGCACGTTATTTTGCAGATA

AACGTCGTCCGCGTGGTCGTGCACAGTTTGATGTT

GTTGATTGGCAGCCTGGTCCGCATACAGGTGCACC

GCTGCTGAGCGGTGCGCTGGCATGGCTGGAATGTG

AAGTTGCACAGTGGCATGAAGGTGGCGATCATACC

ATTTTTCTGGGTCGTGTTCTGGGTTGTCGTCGTGG

TCCGGATAGTCCGGCACTGCTGTTTTATGGTAGCG

ATTTTCATCAGATCCGCTAA

-continued

Seq ID #14:
SeFR AA
Organism: *Saccharothrix espanaensis*
MMTVYDSALTMEETTLRDAMSRFATGVSVVTVGGE

HTHGMTANAFTCVSLDPPLVLCCVARKATMHAAIE

GARRFAVSVMGGDQERTARYFADKRRPRGRAQFDV

VDWQPGPHTGAPLLSGALAWLECEVAQWHEGGDHT

IFLGRVLGCRRGPDSPALLFYGSDFHQIR

Seq ID #15:
PfFR NT
Organism: *Pseudomonas fluorescens*
ATGAATGCAGCAACCGAAACCAAAGTTCATGATCT

GCTGGATGCCGAAGGTCGTGATGTTCGTGATGCAC

GTGAACTGCGTAATGTTCTGGGTCAGTTTGCAACC

GGTGTTACCGTTATTACCACCCGTACCGCAGATGG

TCGTAATGTTGGTGTGACCGCAAATAGCTTTAGCA

GCCTGAGCCTGAGTCCGGCACTGGTTCTGTGGTCA

CTGGCACGTACCGCACCGAGCCTGAAAGTTTTTTG

TAGCGCAAGCCATTTTGCCATTAATGTGCTGGGTG

CACATCAGCTGCATCTGAGCGAACAGTTTGCACGT

GCCGCAGCAGATAAATTTGCCGGTGTTGCACATAG

TTATGGTAAAGCGGGTGCACCGGTTCTGGATGATG

TTGTTGCAGTTCTGGTTTGCCGTAATGTTACCCAG

TATGAAGGTGGTGATCATCTGATTTTTATCGGCGA

AATTGAGCAGTATCGTTATAGCGGTGCAGAACCGC

TGGTTTTTCATGCAGGTCAGTATCGTGGTCTGGGT

AGCAATCGTGCAGAAAGCGTTCTGAAACATGAATA

A

Seq ID #16:
PfFR AA
Organism: *Pseudomonas fluorescens*
MNAATETKVHDLLDAEGRDVRDARELRNVLGQFAT

GVTVITTRTADGRNVGVTANSFSSLSLSPALVLWS

LARTAPSLKVFCSASHFAINVLGAHQLHLSEQFAR

AAADKFAGVAHSYGKAGAPVLDDVVAVLVCRNVTQ

YEGGDHLIFIGEIEQYRYSGAEPLVFHAGQYRGLG

SNRAESVLKHE

Seq ID #17:
HpaC NT
Organism: *Escherichia coli*
ATGCAATTAGATGAACAACGCCTGCGCTTTCGTGA

CGCAATGGCCAGCCTGTCGGCAGCGGTAAATATTA

TCACCACCGAGGGCGACGCCGGACAATGCGGGATT

-continued

ACGGCAACGGCCGTCTGCTCGGTCACGGATACACC

ACCATCGCTGATGGTGTGCATTAACGCCAACAGTG

CGATGAACCCGGTTTTTCAGGGCAACGGTAAGTTG

TGCGTCAACGTCCTCAACCATGAGCAGGAACTGAT

GGCACGCCACTTCGCGGGCATGACAGGCATGGCGA

TGGAAGAGCGTTTTAGCCTCTCATGCTGGCAAAAA

GGTCCGCTGGCGCAGCCGGTGCTAAAAGGTTCGCT

GGCCAGTCTTGAAGGTGAGATCCGCGATGTGCAGG

CAATTGGCACACATCTGGTGTATCTGGTGGAGATT

AAAAACATCATCCTCAGTGCAGAAGGTCACGGACT

TATCTACTTTAAACGCCGTTTCCATCCGGTGATGC

TGGAAATGGAAGCTGCGATTTAA

-continued

Seq ID #18:
HpaC AA
Organism: *Escherichia coli*
MQLDEQRLRFRDAMASLSAAVNIITTEGDAGQCGI

TATAVCSVTDTPPSLMVCINANSAMNPVFQGNGKL

CVNVLNHEQELMARHFAGMTGMAMEERFSLSCWQK

GPLAQPVLKGSLASLEGEIRDVQAIGTHLVYLVEI

KNIILSAEGHGLIYFKRRFHPVMLEMEAAI

Seq ID #19
NT
Artificial Sequence; N-terminal tag
ATGACGACCGCTAGTGGTACCAATGCAGATGTCCA

GAATGGCGTCCGCCCG

Seq ID #20
AA
Artificial Sequence; N-terminal tag
MTTASGTNADVQNGVRP

The invention claimed is:

1. A method of producing a 3'-hydroxylated flavonoid, the method comprising incubating a transformed host cell in a suitable medium comprising a flavonoid for a sufficient time to convert said flavonoid to a 3'-hydroxylated flavonoid, wherein the transformed host cell comprises a synthetic or recombinant nucleic acid molecule comprising a first polynucleotide sequence that encodes a flavonoid 3'-hydroxylase, said flavonoid 3'-hydroxylase comprising: i) an amino acid sequence having at least 85% sequence identity to the amino acid sequence of SEQ ID NO: 12, ii) the amino acid sequence of SEQ ID NO: 20, or iii) an amino acid sequence having at least 80% sequence identity to the amino acid sequence of SEQ ID NO: 12 and the amino acid sequence of SEQ ID NO: 20.

2. The method of claim 1, wherein said flavonoid 3'-hydroxylase comprises an amino acid sequence having at least 90% sequence identity to the amino acid sequence of SEQ ID NO: 12.

3. The method of claim 1, wherein said flavonoid 3'-hydroxylase comprises the amino acid sequence of SEQ ID NO: 20.

4. The method of claim 1, wherein said flavonoid 3'-hydroxylase comprises the amino acid sequence of SEQ ID NO: 2, SEQ ID NO: 4, SEQ ID NO: 6, SEQ ID NO: 8, or SEQ ID NO: 10.

5. The method of claim 4, wherein the first polynucleotide sequence comprises a nucleic acid sequence having at least 80% sequence identity to the nucleic acid sequence of SEQ ID NO: 1, SEQ ID NO: 3, SEQ ID NO: 5, SEQ ID NO: 7, or SEQ ID NO: 9.

6. The method of claim 1, wherein the nucleic acid molecule further comprises a second polynucleotide sequence that encodes a flavin reductase.

7. The method of claim 6, wherein the flavin reductase is a polypeptide comprising the amino acid sequence of SEQ ID NO: 14, SEQ ID NO: 16, or SEQ ID NO: 18.

8. The method of claim 1, wherein the flavonoid has the generic structure of one of the following:

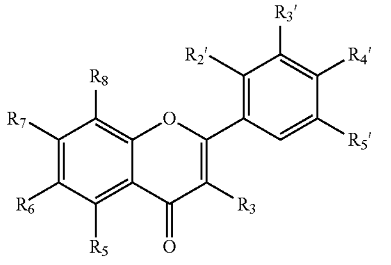

Flavone

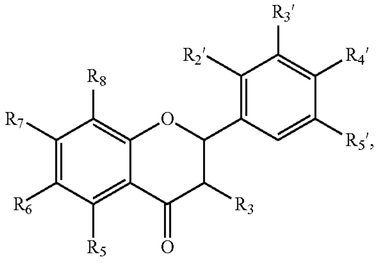

Flavanone wherein $R_{3'}$ is H, and each of $R_{2'}$, $R_{4'}$, $R_{5'}$, $R_3$, $R_5$, $R_6$, $R_7$, and $R_8$ independently, is selected from the group consisting of H, OH, and $OCH_3$, and wherein $R_{3'}$ is OH in the 3'-hydroxylated flavonoid and each of $R_{2'}$, $R_{4'}$, $R_{5'}$, $R_3$, $R_5$, $R_6$, $R_7$, and $R_8$ in the 3'-hydroxylated flavonoid is identical to the flavonoid.

9. The method of claim 8, wherein the flavonoid is naringenin and the 3'-hydroxylated flavonoid is eriodictyol.

10. The method of claim 4, wherein the flavonoid 3'-hydroxylase encoded by the first polynucleotide sequence comprises the amino acid sequence of SEQ ID NO: 4.

11. The method of claim 7, wherein the flavin reductase encoded by the second polynucleotide sequence comprises the amino acid sequence of SEQ ID NO: 14.

12. The method of claim 1, wherein the host cell is selected from the group of microbial species consisting of *Escherichia; Salmonella; Bacillus; Acinetobacter; Streptomyces; Corynebacterium; Methylosinus; Methylomonas;*

*Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea*; and *Clostridium.*

13. An isolated recombinant host cell transformed with a nucleic acid construct comprising a first polynucleotide sequence encoding a flavonoid 3'-hydroxylase comprising: i) an amino acid sequence having at least 85% sequence identity to the amino acid sequence of SEQ ID NO: 12, ii) the amino acid sequence of SEQ ID NO: 20, or iii) an amino acid sequence having at least 80% sequence identity to the amino acid sequence of SEQ ID NO: 12 and the amino acid sequence of SEQ ID NO: 20.

14. The host cell of claim 13, wherein said flavonoid 3'-hydroxylase comprises an amino acid sequence having at least 90% sequence identity to the amino acid sequence of SEQ ID NO: 12.

15. The host cell of claim 13, wherein said flavonoid 3'-hydroxylase comprises the amino acid sequence of SEQ ID NO: 20.

16. The host cell of claim 13, wherein said flavonoid 3'-hydroxylase comprises the amino acid sequence of SEQ ID NO: 2, SEQ ID NO: 4, SEQ ID NO: 6, SEQ ID NO: 8, or SEQ ID NO: 10.

17. The host cell of claim 16, wherein the first polynucleotide sequence comprises a nucleic acid sequence having at least 80% sequence identity to the nucleic acid sequence of SEQ ID NO: 1, SEQ ID NO: 3, SEQ ID NO: 5, SEQ ID NO: 7, or SEQ ID NO: 9.

18. The host cell of claim 13, wherein the nucleic acid construct further comprises a second polynucleotide sequence encoding a flavin reductase.

19. The host cell of claim 18, wherein the flavin reductase is a polypeptide comprising the amino acid sequence of SEQ ID NO: 14, SEQ ID NO: 16, or SEQ ID NO: 18.

20. The host cell of claim 13, wherein the nucleic acid construct comprises a first polynucleotide sequence encoding a flavonoid 3'-hydroxylase comprising the amino acid sequence of SEQ ID NO: 4 and a second polynucleotide sequence encoding a flavin reductase comprising the amino acid sequence of SEQ ID NO: 14.

21. The host cell of claim 13, wherein the host cell is selected from the group of microbial species consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea*; and *Clostridium.*

* * * * *